(12) United States Patent
Panzner et al.

(10) Patent No.: US 9,677,078 B2
(45) Date of Patent: Jun. 13, 2017

(54) CARBOXYLATED POLYAMINE DERIVATIVES AS TRANSFECTION REAGENTS

(71) Applicant: Lipocalyx GmbH, Halle (DE)

(72) Inventors: Steffen Panzner, Halle (DE); Christian Reinsch, Halle (DE); Volkmar Wendisch, Dessau (DE); Christina Dreher, Halle (DE)

( * ) Notice: Subject to any disclaimer, the term of this patent is extended or adjusted under 35 U.S.C. 154(b) by 0 days.

(21) Appl. No.: 14/432,361

(22) PCT Filed: Oct. 2, 2013

(86) PCT No.: PCT/EP2013/002979
§ 371 (c)(1),
(2) Date: Mar. 30, 2015

(87) PCT Pub. No.: WO2014/056590
PCT Pub. Date: Apr. 17, 2014

(65) Prior Publication Data
US 2015/0275220 A1    Oct. 1, 2015

(30) Foreign Application Priority Data

Oct. 8, 2012  (EP) .................................... 12006963

(51) Int. Cl.

| | | |
|---|---|---|
| C12N 15/64 | (2006.01) | |
| C08F 8/14 | (2006.01) | |
| C08F 8/18 | (2006.01) | |
| C08G 73/02 | (2006.01) | |
| C08G 81/00 | (2006.01) | |
| C08K 5/205 | (2006.01) | |
| C08L 39/00 | (2006.01) | |
| C08L 39/02 | (2006.01) | |
| C12N 15/113 | (2010.01) | |
| C12N 15/85 | (2006.01) | |
| A61K 47/48 | (2006.01) | |
| C08L 79/02 | (2006.01) | |

(52) U.S. Cl.
CPC ........ *C12N 15/64* (2013.01); *A61K 47/48038* (2013.01); *A61K 47/48046* (2013.01); *A61K 47/48192* (2013.01); *A61K 47/48315* (2013.01); *C08F 8/14* (2013.01); *C08F 8/18* (2013.01); *C08G 73/0206* (2013.01); *C08G 81/00* (2013.01); *C08K 5/205* (2013.01); *C08L 39/00* (2013.01); *C08L 39/02* (2013.01); *C08L 79/02* (2013.01); *C12N 15/1137* (2013.01); *C12N 15/85* (2013.01); *C08L 2203/02* (2013.01); *C12N 2310/14* (2013.01); *C12N 2310/351* (2013.01); *C12N 2800/107* (2013.01)

(58) Field of Classification Search
None
See application file for complete search history.

(56) References Cited

U.S. PATENT DOCUMENTS

2003/0077827 A1    4/2003  Uhler

FOREIGN PATENT DOCUMENTS

| CN | 202305540 | 7/2012 |
|---|---|---|
| WO | WO9859064 A1 | 12/1998 |
| WO | WO 01/66149 A2 | 9/2001 |
| WO | WO0176643 A1 | 10/2001 |
| WO | WO 02/42447 A2 | 5/2002 |
| WO | WO2007006700 A1 | 1/2007 |
| WO | WO 2007/132873 A1 | 11/2007 |
| WO | WO 2009-125986 A2 | 10/2009 |
| WO | WO2011120953 A1 | 10/2011 |

OTHER PUBLICATIONS

Incani, V., et al., "Lipid and hydrophobic modification of cationic carriers on route to superior gene vectors", Soft Matter, vol. 6, No. 10, Jan. 2010, pp. 2124-2138.
Philipp, A., et al., "Functional modification of amide-crosslinked oligoethylenimine for improved siRNA delivery", Reactive & Functional Polymers, Elsevier Science Publishers VV, NL, vol. 71, No. 3, Oct. 2010.
Reza K. Oskuee et al., "Alkylcarboxylate grafting to polyethylenimine: a simple approach to producing a DNA nanocarrier with low toxicity", The Journal of Gene Medicine, vol. 11, No. 10, Oct. 1, 2009, pp. 921-932.
PCT/EP2013/002979 International Search Report and Written Opinion dated Nov. 29, 2013.
Dehshahri a et al: "Gene transfer efficiency of high primary amine content, hydrophobic, alkyl-oligoamine derivatives of polyethylenimine", Biomaterials; Elsevier Science Publishers BV., Barking, GB. vol. 30, No. 25, Sep. 1, 2009.
Ali Dehshahri, et al.: "Gene transfer efficiency of high primary amine content, . . .", Biomaterials 30(2009), pp. 4187-4194.

*Primary Examiner* — Robert M Kelly
(74) *Attorney, Agent, or Firm* — Polsinelli PC

(57) ABSTRACT

The invention provides polyamine derivatives, a use of the polyamine derivatives for the transfection of polyanions into cells, and a method of transfecting cells with a polyanion, comprising mixing said polyanion with a polyamine derivative e.g. in a buffer and treating said cells with the mixture obtained in the previous step.

23 Claims, 2 Drawing Sheets

Fig. 1

|   | 1 | 2 | 3 | 4 | 5 | 6 | 7 | 8 | 9 | 10 | 11 | 12 |
|---|---|---|---|---|---|---|---|---|---|----|----|----|
| A | 100 | 100 | 100 | 100 | 100 | 100 | 100 | 100 | 100 | 100 | 100 | 100 |
| B | 100 | 100 | 100 | 100 | 100 | 100 | 100 | 100 | 100 | 100 | 100 | 100 |
| C | 100 | 100 | 100 | 100 | 100 | 100 | 100 | 100 | 100 | 100 | 100 | 100 |
| D | 100 | 100 | 100 | 100 | 100 | 100 | 100 | 100 | 100 | 100 | 100 | 100 |
| E | 100 | 100 | 100 | 100 | 100 | 100 | 100 | 100 | 100 | 100 | 100 | 100 |
| F | 100 | 100 | 100 | 100 | 100 | 100 | 100 | 100 | 100 | 100 | 100 | 100 |
| G | 100 | 100 | 100 | 100 | 100 | 100 | 100 | 100 | 100 | 100 | 100 | 100 |
| H | 100 | 100 | 100 | 100 | 100 | 100 | 100 | 100 | 100 | 100 | 100 | 100 |

Fig. 2

|   | 1 | 2 | 3 | 4 | 5 | 6 | 7 | 8 | 9 | 10 | 11 | 12 |
|---|---|---|---|---|---|---|---|---|---|----|----|----|
| A | 50 | 50 | 50 | 50 | 50 | 50 | 50 | 50 | 50 | 50 | 50 | 50 |
| B | 75 | 75 | 75 | 75 | 75 | 75 | 75 | 75 | 75 | 75 | 75 | 75 |
| C | 110 | 110 | 110 | 110 | 110 | 110 | 110 | 110 | 110 | 110 | 110 | 110 |
| D | 170 | 170 | 170 | 170 | 170 | 170 | 170 | 170 | 170 | 170 | 170 | 170 |
| E | 50 | 50 | 50 | 50 | 50 | 50 | 50 | 50 | 50 | 50 | 50 | 50 |
| F | 75 | 75 | 75 | 75 | 75 | 75 | 75 | 75 | 75 | 75 | 75 | 75 |
| G | 110 | 110 | 110 | 110 | 110 | 110 | 110 | 110 | 110 | 110 | 110 | 110 |
| H | 170 | 170 | 170 | 170 | 170 | 170 | 170 | 170 | 170 | 170 | 170 | 170 |

Fig. 3

|   | 1   | 2 | 3 | 4 | 5   | 6 | 7 | 8 | 9   | 10 | 11 | 12 |
|---|-----|---|---|---|-----|---|---|---|-----|----|----|----|
| A | 100 | 0 | 0 | 0 | 100 | 0 | 0 | 0 | 100 | 0  | 0  | 0  |
| B | 100 | 0 | 0 | 0 | 100 | 0 | 0 | 0 | 100 | 0  | 0  | 0  |
| C | 100 | 0 | 0 | 0 | 100 | 0 | 0 | 0 | 100 | 0  | 0  | 0  |
| D | 100 | 0 | 0 | 0 | 100 | 0 | 0 | 0 | 100 | 0  | 0  | 0  |
| E | 100 | 0 | 0 | 0 | 100 | 0 | 0 | 0 | 100 | 0  | 0  | 0  |
| F | 100 | 0 | 0 | 0 | 100 | 0 | 0 | 0 | 100 | 0  | 0  | 0  |
| G | 100 | 0 | 0 | 0 | 100 | 0 | 0 | 0 | 100 | 0  | 0  | 0  |
| H | 100 | 0 | 0 | 0 | 100 | 0 | 0 | 0 | 100 | 0  | 0  | 0  |

Fig. 4

|   | 1   | 2 | 3 | 4 | 5   | 6 | 7 | 8 | 9   | 10 | 11 | 12 |
|---|-----|---|---|---|-----|---|---|---|-----|----|----|----|
| A | 50  | 0 | 0 | 0 | 50  | 0 | 0 | 0 | 50  | 0  | 0  | 0  |
| B | 75  | 0 | 0 | 0 | 75  | 0 | 0 | 0 | 75  | 0  | 0  | 0  |
| C | 110 | 0 | 0 | 0 | 110 | 0 | 0 | 0 | 110 | 0  | 0  | 0  |
| D | 170 | 0 | 0 | 0 | 170 | 0 | 0 | 0 | 170 | 0  | 0  | 0  |
| E | 50  | 0 | 0 | 0 | 50  | 0 | 0 | 0 | 50  | 0  | 0  | 0  |
| F | 75  | 0 | 0 | 0 | 75  | 0 | 0 | 0 | 75  | 0  | 0  | 0  |
| G | 110 | 0 | 0 | 0 | 110 | 0 | 0 | 0 | 110 | 0  | 0  | 0  |
| H | 170 | 0 | 0 | 0 | 170 | 0 | 0 | 0 | 170 | 0  | 0  | 0  |

CARBOXYLATED POLYAMINE DERIVATIVES AS TRANSFECTION REAGENTS

CROSS REFERENCE TO RELATED APPLICATIONS

This application is a national phase application of PCT/EP2013/002979, filed Oct. 2, 2013 which claims priority to European Patent Application No. 12006963.8, filed Oct. 8, 2012. The contents of all these applications are expressly incorporated herein by reference in their entireties.

FIELD OF THE INVENTION

The invention relates to polyamine derivatives and to the use of polyamine derivatives for the transfection of nucleic acids and other polyanions into cells. The invention also relates to a method for the transfection of polyanions into cells, and to kits and polyamine derivatives therefor. The polyamine derivatives of the invention are effective transfectants with very low toxicity that can be used for transfecting a broad range of different cell types.

STATE OF THE ART

Transfection is the introduction of foreign matter into cells. Within the context of transfection, "into cells" means transport of the foreign matter across at least one biological membrane. Further transport may occur into cellular compartments or organelles. In contrast, a mere inclusion of the material into endosomes, pinocytic or phagocytic vesicles or lysosomes is not considered a transfection.

The foreign matter may encompass molecules such as peptides, proteins and various types of nucleic acids; the latter can be as small as oligonucleotides or as long as plasmids. It may also include assemblies of such molecules. In any case the molecules or assemblies are large and hydrophilic, two features which prevent their unassisted cellular uptake. Transfection therefore requires the use of specific helper reagents. Amongst others, polyamines can be such reagents. Polyamines form polycations in solution, which facilitates the complex formation with polyanions such as nucleic acids. These complexes are the actual transfection competent entities.

Transfection of complexes from a polyamine and a plasmid was demonstrated by Boussif et al (Proc Natl Acad Sci USA (1995), 92(16):7297-7301) or in U.S. Pat. No. 6,013,240), using branched polyethyleneimine (PEI) as the polyamine. While keeping the concept, others sought to improve the technology by various means. Strategies for improving transfectants include (i) selection of a specific size or configuration of the polycation, such as linear PEI of a certain length (WO2009/016507);

(ii) use of metabolically labile multimeres of such polycations (Gosselin et al. (2001) Bioconj Chem, 12(6):989-994; Lynn et al (2001) J Am Chem Soc 123(33):8155-8156; WO2007/020060 to Gopfrich et al.; WO2007/120479 to Tanaka et al.);

(iii) employment of lipid admixtures (U.S. Pat. No. 7,601,367 to Monahan et al.) or (iv) chemical modifications of the polymer backbone, e.g. grafting of aromatic amino acids (in WO2009/074970 to Adib et al.), grafting of histidine or imidazol moieties (in WO 2009/011402), alkylations as in Wakefield et al. (2005) Bioconj Chem 16(5):1204-1208 or the modification with cholesterol (in US2007/0154447 to Ferguson et al).

The hydrophobic modifications improve the membrane penetration of a transfectant (see Wakefield et al.) but are associated with a lower stability of the complex in solution; the formulated material tends to form aggregates. Grafting of polyethyleneglycol (PEG) (by Matar et al. in WO2009/021017 or in Rozema et al (2007) Proc Natl Acad Sci USA 104(32):12982-12987) counteracts aggregation but on the flip side competes with the biological activity and must be reversible as shown in the Rozema publication.

As it is evident from the many different strategies and from the large number of reports, the development of novel transfectants is a topic of intense research. Their use has substantial commercial relevance; transfection reagents had a market volume of about 200 Mio USD in 2011 (Frost & Sullivan, Global Transfection Markets, N6F0-01).

The two most important criteria in the development and improvement of transfectants are (i) a high signal-to-noise ratio and (ii) efficient transfection across a large number of different cell types. The signal-to-noise ratio describes the effect of the transfection complex compared to the transfectant alone or in comparison with a transfection complex comprising an irrelevant nucleic acid.

It is therefore an objective of the invention to provide a transfectant for transfecting polyanions into cells and a method of transfecting cells. It is another objective to provide a transfectant that is superior to commercially available materials in the criteria (a) and/or (b). Given the large number and diversity of approaches used before, no specific rationale could be identified that would have guided such invention.

BRIEF DESCRIPTION OF THE INVENTION

The above objectives are achieved by:

(1) Use of a polyamine derivative for the transfection of polyanions into cells, said polyamine comprising:

a polyamine moiety comprising a plurality of amino groups;

a plurality of carboxylated substituents comprising a carboxyl group bonded via a hydrophobic linker to amino groups of said polyamine moiety; and a plurality of hydrophobic substituents bonded to amino groups of said polyamine moiety;

said hydrophobic linker having a log P of from 3 to 20 determined for a compound obtainable from said linker by replacing bonds of said linker to the carboxyl group and the amino group of said polyamine by bonds to hydrogen atoms; and said hydrophobic substituent having a log P of from 1.5 to 20 determined for a compound obtainable from said hydrophobic substituent by replacing the bond of said hydrophobic substituent to an amino group of said polyamine moiety by a bond to a hydrogen atom.

(2) Use of a polyamine derivative for the transfection of polyanions into cells, said polyamine comprising:

a polyamine moiety comprising a plurality of amino groups;

a plurality of carboxylated substituents comprising a carboxyl group bonded via a hydrophobic linker to amino groups of said polyamine moiety, wherein each of said carboxylated substituents comprises from 6 to 40 carbon atoms, preferably from 6 to 20 carbon atoms, and more preferably from 8 to 16 carbon atoms, and each of said hydrophobic linker may comprise from 1 to 3 heteroatoms selected from O, N, and S; and a plurality of hydrophobic substituents bonded to amino groups of said polyamine moiety, wherein each of said hydrophobic substituents comprises at least 2 carbon atoms, preferably from 6 to 40 carbon atoms, and may comprise from 1 to 3 heteroatoms selected from O, N, and S provided said hydrophobic substituent has at least 6 carbon atoms.

(3) The use according to item 1 or 2, wherein each of said carboxylated substituents of said polyamine derivative comprises any one or more of the following moieties as said hydrophobic linker: alkylene, alkenylene, alkynylene, cycloalkylene, cycloalkenylene, arylene, and combinations thereof; and/or each of said hydrophobic substituents of said polyamine derivative comprises any one or more of the following moieties: alkyl, alkenyl, alkynyl, cycloalkyl, cycloalkenyl, aryl, and combinations thereof.

(4) Polyamine derivative as defined in item 1 or 2.

(5) Polyalkylenimine derivative having one or more carboxyalkyl substituents comprising from 6 to 40 carbon atoms, and one or more hydrophobic substituents selected from hydrocarbon substituents having at least 2 carbon atoms, preferably from 6 to 40 carbon atoms, wherein each of said hydrophobic substituents may be or may comprise an alkyl group and/or each of said hydrophobic substituents may be or may comprise an aryl group.

(6) The polyalkylenimine derivative according to item 5, wherein the carboxyalkyl substituents and the hydrophobic substituents in said polyalkylenimine derivative have a molar ratio of from 10:1 to 0.1:1 (the C/A ratio), preferably the C/A ratio of these groups is from 3:1 to 0.33:1.

(7) The polyamine derivative or polyalkylenimine derivative according to any one of items 4 to 6, wherein said carboxylated substituents are all the same and said hydrophobic substituents are all the same, and the sum of carbon atoms in one of said carboxylated substituents plus those in one of said hydrophobic substituents is from 10 to 30, preferably from 15 to 25.

(8) Complex of a nucleic acid or a protein with the polyamine derivative of the invention.

(9) A kit comprising:
(i) a polyamine derivative as defined herein,
(ii) a buffer solution having a pH between 4 and 8, and
(iii) optionally a manual with instructions for use.

(10) A method of transfecting cells with a nucleic acid or a protein, comprising mixing said nucleic acid or a protein with a polyamine derivative as defined herein e.g. in an aqueous buffer and treating said cells with the mixture obtained in the previous step.

(11) A container comprising multiple compartments containing a lyophilized composition comprising a transfectant, said transfectant may be or may comprise the polyamine derivative as defined in any one of items 1 to 7.

The invention also provides:

(12) A use of a carboxyalkyl-alkyl-polyamine for the transfection of polyanions into cells.

(13) The use according to item 12, wherein the polyamine moiety of said carboxyalkyl-alkyl-polyamine is selected from the group consisting of polyalkylenimines, polyallyamines, polyvinylamines, polylysines and polyornithins, wherein said polyalkylenimines preferably are polyethylenimines, polypropylenimines, polybutylenimines or oligospermines or homologues thereof, and wherein said polyamine moiety comprises between 12 and 100000 nitrogen atoms, more preferably between 20 and 5000 nitrogen atoms.

(14) The use according to any one of items 12 or 13, wherein the carboxyalkyl moiety is an aliphatic carboxyalkyl moiety having between 4 and 40 carbon atoms, preferably between 6 and 20 carbon atoms and more preferably between 8 and 16 carbon atoms.

(15) The use according to any one of items 12 to 14, wherein the alkyl moiety is an aliphatic alkyl moiety having at least 2 carbon atoms, preferably between 6 and 40 carbon atoms.

(16) The use according to any one of items 12 to 15, wherein all carboxyalkyl moieties of said carboxyalkyl-alkyl-polyamine are the same and all alkyl moieties are the same, and the sum of carbon atoms in the carboxyalkyl moiety and the alkyl moiety is between 10 and 30, preferably between 15 and 25.

(17) The use according to any one of items 12 to 16, wherein said carboxyalkyl-alkyl-polyamine is a linear carboxyalkyl-alkyl-polyalkylenimine comprising structural units of the following formula (6)

wherein x is an integer of from 1 to 10, wherein the value of x may be the same or different among different groups $(CH_2)_x$,
$R^6$ is hydrogen, $C_rH_{2r+1}$ or $C_{s-1}H_{2s-2}COOH$
r is an integer of from 2 to 40,
s is an integer of from 4 to 40;
or
wherein said carboxyalkyl-alkyl-polyamine is a branched carboxyalkyl-alkyl-polyalkylenimine comprising structural units of each of the formulae (7), (8) and (9):

wherein
$R^6$, x, r and s are as defined above and
$R^7$ comprises one or more units selected from the formulae (7), (8) and (9);
y is an integer of from 1 to 10, preferably of from 2 to 10, wherein the value of y may be the same or different among multiple occurrences of groups $(CH_2)_y$;
and wherein the number of nitrogen atoms per molecule of said linear or said branched carboxyalkyl-alkyl-polyalkylenimine is between 12 and 100000.

(18) The use according to any one of items 12 to 17, wherein the molar ratio of carboxyalkyl moieties to alkyl moieties in said carboxyalkyl-alkyl-polyamine is within the range of from 6:1 to 0.33:1, preferably of from 2:1 to 0.5:1.

(19) The use according to any one of items 12 to 18, wherein at least 10 mol %, preferably between 25 and 80 mol %, more preferably between 30 and 60 mol % of amino groups of said polyamine are substituted by said carboxyalkyl and said alkyl groups (degree of substitution).

(20) The use of according to any one of items 12 to 19, wherein the polyanions are nucleic acids.

(21) The polyalkylenimine derivative according to item 5, which is a carboxyalkyl-alkyl-polyamine, wherein said carboxyalkyl-alkyl-polyamine has one type of carboxyalkyl moiety and one type of alkyl moiety, and the sum of carbon atoms in the type of carboxyalkyl moiety and the type of alkyl moiety is between 10 and 30, preferably between 15 and 25.

(22) The polyalkylenimine derivative according to items 21, wherein said polyalkylenimine derivative is a branched polyethylenimine, wherein further said carboxylalkyl moiety has between 8 and 16 carbon atoms and wherein said alkyl moiety has from 8 to 10, preferably about 9, carbon atoms.

(23) Complex of a nucleic acid with a carboxyalkyl-alkyl-polyamine as defined in any one of the preceding items 12 to 22.

(24) A kit comprising:

(i) a carboxyalkyl-alkyl-polyamine as defined in any one of items 12 to 19 or 21 to 22, (ii) a buffer solution having a pH between 4 and 8 and an ionic strength of 0.2 mol/L or less, preferably of 0.1 mol/L or less, and (iii) optionally a manual with instructions for use.

(25) The kit of item 24, wherein said polyamine is provided as a solution and wherein the solvent is a lower alcohol selected from the group of ethanol, propanol, 1,2-dihydroxy-propane or isopropanol, or mixtures comprising water and between 33 and 100% of such lower alcohol.

(26) The kit of item 24, wherein said polyamine is provided in dry form.

(27) The kit of items 24 or 26, wherein said polyamine is provided in lyophilized form.

(28) The kit of any one of items 24 to 27, wherein said polyamine is deposited in a multi-well plate.

(29) A kit as in item 28, wherein the wells of said multi-well plate contain different amounts of said polyamine, preferably gradients of said polyamines in neighboring wells or wherein certain wells are empty.

(30) A method of transfecting cells with a polyanion, comprising mixing said polyanion with a carboxyalkyl-alkyl-polyamine as defined in any one of items 12 to 22 in water or an aqueous buffer and treating said cells with the mixture obtained in the previous step.

Polyamines were chemically modified with carboxylated substituents comprising a carboxyl group bonded via a hydrophobic linker to a polyamine, and with hydrophobic substituents. The modified polyamines used in the present invention are denoted as carboxylated, hydrophobized polyamines or as modified polyamines or as polyamine derivatives throughout this description. In one embodiment, polyamines were chemically modified with carboxyalkyl substituents and alkyl substituents. These modified polyamines are denoted as carboxyalkyl-alkyl-polyamines herein. It was surprisingly found that a combination of both modifications was superior to any of the single modifications as a high signal-to-noise ratio and more effective transfection were achieved. The novel reagents feature these results on numerous cell types and are also superior to commercially available materials and those described in the state of the art.

DETAILED DESCRIPTION OF THE INVENTION

The polyamine derivative of this invention has carboxylated substituents and hydrophobic substituents on a polyamine, wherein these substituents may comprise, independently from each other, one, two or three heteroatoms selected from oxygen, nitrogen or sulfur. The carboxyalkyl-alkyl-polyamine of the invention is a polyamine derivative that has carboxyalkyl substituents as said carboxylated substituents and alkyl substituents as said hydrophobic substituents on a polyamine.

The polyamine derivative of the invention is obtainable by methods known in the art. One possible procedure is the derivatization of a polyamine with a halogenated carboxylic acid that forms said carboxylated substituent upon nucleophilic substitution of the halogen by an amino group of the polyamine, and with a halogenated hydrophobic compound that forms said hydrophobic substituent upon nucleophilic substitution of the halogen by an amino group of the polyamine. The carboxyalkyl-alkyl-polyamine of the invention is obtainable analogously. One possible procedure is the alkylation of a polyamine with a haloalkanoic acid and with a haloalkane by nucleophilic substitution. The halogen or halo substituents may be chlorine, bromine or iodine atoms, preferably they are bromine. More details on the preparation of the polyamine derivative and the carboxyalkyl-alkyl-polyamine are given below.

Polyamines

The polyamine that can be used as a starting material for producing the polyamine derivative of the invention is a polymeric compound having a plurality of nitrogen atoms that form plural amino groups. These nitrogen atoms can become charged in aqueous solutions by protonation. Most aliphatic amines have a pK greater than 8 or 9 which means they are substantially or completely charged in aqueous solutions having a pH around 7.4, which is the physiological pH, or at lower pH values.

Amine moieties having a pK below 6, e.g. pyridines or anilines, are less preferred amino groups of the polyamine. The pK values of the various amines are easily available as they are frequently cited in the respective articles of the English Wikipedia found at en.wikipedia.org or they can be calculated using software, e.g. ACD/pKa database (Advanced Chemistry Development, Ontario, Canada).

The plural nitrogen atoms of the polyamines can be primary, secondary, tertiary and/or quaternary amino groups, they may also be part of ring systems. Primary, secondary, tertiary and/or quaternary amino groups may occur in the same polyamine molecule. Primary, secondary, tertiary amino groups are preferred, since they can be alkylated as described above. The polyamines may further comprise end groups (terminal groups) that may also be amino groups; however, such end groups may also be initiators or termination groups from the polymerization reaction that was used to make the polyamine.

In the case of certain linear polyamines, the internal amino groups may be secondary amino groups; examples of such polyamines are polyalkylenimines. In other linear polyamines, the amino groups are not part of the polymer backbone but of side chains or they form the side chain by itself. In the case of branched polyamines, internal amino groups that form branching points are generally tertiary amino groups, while internal amino groups that are not branching points are generally secondary amino groups. Branches of such polymers are often terminated by primary amino groups.

In the following, the polyamines that may be used for producing the polyamine derivative, notably the carboxyalkyl-alkyl-polyamine, of the invention are described. Thereafter, the polyamine derivative and the carboxyalkyl-alkyl-polyamine of the invention are described.

In a first general embodiment, plural nitrogen atoms of the polyamine usable for preparing the polyamine derivative and the carboxyalkyl-alkyl-polyamine of the invention are part of the polymeric backbone of the polyamine. The polyamine may be a linear polyamine having the plural nitrogen atoms within the polymer chain. Such polyamine may be a polyalkylenimine comprising plural units of formula (1):

$$—[CH_2—NR^1—(CH_2)_x]— \tag{1}$$

wherein x is an integer of from 1 to 10 and $R^1$ is hydrogen. In one embodiment, x may be an integer of from 1 to 5, preferably 1 or 2 or 3. The value of x may be the same or different among different groups $(CH_2)_x$ in the same polyamine molecule. For example, x may oscillate between two or three different values of x along the polymer chain of the polyamine, such as between values of x of 2 and 3, between values of 2 and 4, or between values 2 and 5. In the polyamines of formula (1), essentially all amino groups within the polymer chain are secondary amino groups.

If m is the number of repetitive units of formula (1) in the polyalkylenimine, m may be an integer of from 12 to 100000, preferably from 12 to 20000, more preferably from 20 to 10000, most preferably of from 20 to 5000.

Examples of polyamines that become the polyamine moiety of said polyamine derivative by alkylation, notably by nucleophilic substitution, are polyalkylenimines, preferably polyethylenimines, polypropylenimines, polybutylenimines or oligospermines or homologues thereof. The polyamine moiety may comprise from 12 to 20000 nitrogen atoms, more preferably from 20 to 10000 nitrogen atoms per polyamine molecule, or as defined above for m.

Alternatively, the polyamine that may become the polyamine moiety of said polyamine derivative by alkylation, notably by nucleophilic substitution, may be a branched polyamine, preferably a branched polyalkylenimine. Such branched polyalkylenimine may be defined by having structural units of each of the following formulae (2) to (4):

  (2)

  (3)

  (4)

wherein
$R^1$ and x are as defined above;
$R^2$ comprises units of formula (2), (3) and/or of formula (4);
$R^3$ represents hydrogen; and
y is an integer of from 1 to 10, wherein the value of y may be the same or different among different groups $(CH_2)_y$.

In the branched polyalkylenimine, a main chain thereof may be formed by the divalent units of formula (2) comprising secondary amino groups. In addition, the branched polyalkylenimine, notably a main chain thereof, comprises at least 1 unit of formula (3) that comprises the tertiary nitrogen bound to $R^2$ as a branching point. Branching polymer chains comprise at least one, generally multiple, unit(s) of formula (2), and may further comprise one or more units of formula (3), leading to further branching. Thus, the branched polyalkylenimine may be a dendrimer or a dendronized polymer. In many cases these branched polyalkylenimines comprise the structural elements (2), (3) and (4) in a random sequence leading to irregular structures or random polyamines. The monovalent group of formula (4) defines end groups of the polyalkylenimine that may be present on a main chain as well as on branch chains. Multiple structures of each of formulae (2), (3) and (4) present in the polyalkylenimine may be the same or different in terms of x, $R^2$ and $R^3$.

The degree of branching in the branched polyalkylenimine may be from 1 to 40%, preferably of from 10 to 40%, more preferably of from 15 to 30%. The skilled artisan knows how to quantify the branching of a polymer, e.g. through pH-titrations and quantification of the different compartments of the titration curve or by 1H-NMR measurements.

A measure for the degree of branching in a branched polyalkylenimine is the proportion of primary, secondary and tertiary amino groups. While a linear polyalkylenimine has exclusively secondary amino groups as internal amino groups, branched polyalkylenimines have tertiary amino groups such as of formula (3), the amount of which increases with increasing degree of branching. The molar proportion of primary amino groups in the branched polyamine may be from 1 to 40%, preferably from 15 to 30%. The molar proportion of secondary amino groups may be from 15 to 85%, preferably from 30 to 70%. The molar proportion of tertiary amino groups may be from 1 to 40%, preferably from 15 to 30%.

Examples of branched polyamines that may become the polyamine moiety of said polyamine derivative or of said carboxyalkyl-alkyl-polyamine are branched polyalkylenimines, preferably branched polyethylenimines, branched polypropylenimines, or branched polybutylenimines. The branched polyamines, such as the branched polyalkylenimines, may have between 12 and 100000 nitrogen atoms, more preferably between 20 and 20000 nitrogen atoms per polyamine molecule. In other embodiments, the number of nitrogen atoms in such polymers is between 20 and 5000 nitrogen atoms per molecule of polyamine.

Examples of polyamines having a charged backbone in aqueous medium at neutral pH for use for producing the polyamine derivative or the carboxyalkyl-alkyl-polyamine of the invention are listed in the table 1 below:

TABLE 1

| Polymer | x | number of nitrogen atoms | remarks |
|---|---|---|---|
| Linear polyethylenimine | 1 | 45-75 | Mr 2 . . . 3.1 kDa |
| Linear polyethylenimine | 1 | 450-750 | Mr 20 . . . 31 kDa |
| Linear Polyethylenimine | 1 | 1850-2900 | Mr 80 . . . 125 kDa |
| Linear Polyethylenimine | 1 | 4500-7500 | Mr 200 . . . 310 kDa |
| Branched Polyethylenimine | 1 | 12-17 | Mr 480 . . . 750 Da |
| Branched Polyethylenimine | 1 | 23-35 | Mr 960 . . . 1500 Da |
| Branched Polyethylenimine | 1 | 33-52 | Mr 1440 . . . 2250 Da |
| Branched Polyethylenimine | 1 | 185-290 | Mr 8 . . . 12.5 kDa |
| Branched Polyethylenimine | 1 | 1300-2000 | Mr 56 . . . 87 kDa |
| Branched Polyethylenimine | 1 | 14000-22000 | Mr 600 . . . 950 kDa |
| Branched Polyethylenimine | 1 | 37000-58000 | Mr 1.6 . . . 2.5 MDa |
| Polybutylenimine | 2 | 20-50 | |
| | 2 | 50-200 | |
| | 2 | 200-500 | |
| | 2 | 500-2000 | |
| Oligospermine | 2, 3 alternating | 12-24 | |
| | 2, 3 alternating | 20-32 | |
| | 2, 3 alternating | 28-48 | |
| Oligo(C3, C5)spermine | 2, 4 alternating | 12-24 | |
| | 2, 4 alternating | 20-32 | |
| | 2, 4 alternating | 28-48 | |
| Oligo(C3, C6)spermine | 2, 5 alternating | 12-24 | |
| | 2, 5 alternating | 20-32 | |
| | 2, 5 alternating | 28-48 | |

In Table 1, Mr means relative molecular weight in terms of the number average molecular weight (Mn).

Another example of a branched polyamine is the polyethylenimine of the following structure:

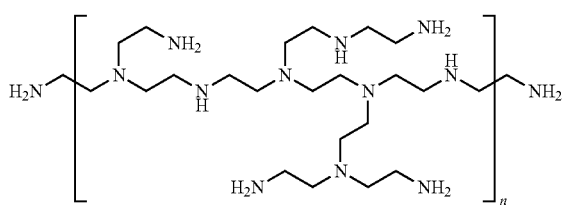

n being an integer such that the number average molecular weight Mn is about 10 000 and having a CAS number 9002-98-6. It is available commercially from Sigma-Aldrich, catalog no. 408727. Other branched polyamines are listed in the examples.

Polyamines may also form multimeric assemblies of polyamine oligomers. Examples for the multimeric assemblies were described in Gosselin et al. (2001) Bioconj Chem, 12(6):989-994; Lynn et al (2001) J Am Chem Soc 123(33): 8155-8156; WO2007/020060 to Gopfrich et al. or WO2007/120479 to Tanaka et al.

In a second general embodiment, the charged nitrogen atoms of the polyamine usable for producing the polyamine derivative or the carboxyalkyl-alkyl-polyamine of the invention are not part of the polymer backbone but are present in side chains of the polyamine. In some embodiments, the polyamine may be derivatives of polyethylene, such as polyallylamine, polyvinylamine, cationized polyacrylate or a polyvinylether of structure (5), $$-[CH_2-CHR^4]_p-, \quad (5)$$

wherein
$R^4$ is selected from $-NH_2$, $-CH_2-NH_2$, $-O-CH_2-CH_2-NH_2$ or $-C(=O)O-R^5$, wherein
$R^5$ is selected from $-CH_2-CH_2-NH_2$, $-CH_2-CH_2-NH-CH_3$, $-CH_2-CH_2-N-(CH_3)_2$, and $-CH_2-CH_2-N-(CH_2-CH_3)_2$.

The variable p is an integer that indicates the size of the polymer and may vary between 20 to about 50000. In preferred embodiments, p is between 20 and 5000, in more preferred embodiments p is between 100 and 2000.

In other embodiments, the polyamines are polypeptides such as polylysines, polyornithins, polyarginines and the like. The number of amino acid residues in these polypeptides may be as defined above for p. In yet other embodiments, the polyamines may have a sugar backbone such as chitosan.

As with the first general embodiment, the polymers of the second general embodiment may also be of linear, branched or of dendrimer type, they may also be multimeric assemblies of polyamine oligomers.

Examples of polyamines having charged side-chains for the second general embodiment are listed in the Table 2 below:

For achieving high performance in transfection, a polyamine such as those described above is modified both with carboxylated substituents and with hydrophobic substituents, e.g. with carboxyalkyl and alkyl substituents, for obtaining the polyamine derivative of the invention. The carboxylated substituents may comprise at least 6 carbon atoms.

Carboxylated Substituents

The carboxylated substituents comprise a carboxyl group bonded via a hydrophobic linker to amino groups of the polyamine, said hydrophobic linker may have a partition coefficient log P of between 3 and 20, preferably from 3 to 10, and more preferably from 4 to 9, determined for a compound obtainable from said linker by replacing bonds of said linker to the carboxyl group and the amino group of the polyamine by bonds to hydrogen atoms. Methods to determine the log P are known to the skilled artisan and comprise the experimental determination of the compound distribution between water and 1-octanol, or obtaining such values from reference sources such as Wikipedia, the English version, or calculating the log P using software such as ACD/Labs 7.0 (Advanced Chemistry Development, Ontario, Canada).

A carboxylated substitutent may comprise one or two carboxyl groups, preferably one carboxyl group. Each carboxylated substitutent comprises from 6 to 40 carbon atoms, preferably from 6 to 20 carbon atoms, and more preferably from 8 to 16 carbon atoms. The hydrophobic linkers of said carboxylated substituents may comprise from 1 to 3, preferably, 1 or 2, heteroatoms selected from O, N, and S. Preferably, the heteroatoms are selected from O and S. In one embodiment, 1 or 2 heteroatoms selected from O, N and S, preferably 0 and S, may be contained in the hydrophobic linker. Thus, the carboxylated substituents may be carboxyhydrocarbyl groups, or they may be carboxyheterohydrocarbyl groups comprising from 1 to 3 heteroatoms selected from O, N, and S, preferably selected from O and S. Among the plurality of carboxylated substituents of a molecule of said polyamine derivative, there may be exclusively carboxyhydrocarbyl groups, exclusively carboxyheterohydrocarbyl groups, or there may be carboxyhydrocarbyl groups and carboxyheterohydrocarbyl groups. In one embodiment, the plurality of carboxylated substituents are all carboxyhydrocarbyl groups. In another embodiment, the plurality of carboxylated substituents are all carboxyheterohydrocarbyl groups.

Where the carboxylated substituents are carboxyhydrocarbyl groups, the hydrocarbyl moieties of said carboxyhydrocarbyl groups may be saturated aliphatic hydrocarbyl moieties, unsaturated aliphatic hydrocarbyl moieties, alicyclic hydrocarbyl moieties, aromatic hydrocarbyl moieties, or moieties comprising two or more moieties from the aforementioned list.

TABLE 2

| Polymer | $R^4$ | $R^5$ | p |
|---|---|---|---|
| Poly-allylamine | $CH_2-NH_2$ | — | 2000 ... 3300 |
| Poly-allylamine | $CH_2-NH_2$ | — | 200-330 |
| Poly-vinylamine | $NH_2$ | — | 450 ... 750 |
| Poly-N-methylvinylamine | $NH-CH_3$ | — | 2000 ... 3300 |
| Poly-(2-(N,N-dimethylamino)ethyl acrylate) | $C(=O)O-R^5$ | $CH_2-CH_2-N-(CH_2-CH_3)_2$ | 280 ... 450 |

Examples of the carboxyhydrocarbyl groups are carboxyalkyl groups, carboxyalkenyl groups, carboxyalkynyl groups, carboxycycloalkyl groups, carboxycycloalkenyl groups, carboxyalkylcycloalkyl groups, carboxycycloalkylalkyl groups, carboxyalkylcycloalkylalkyl groups, carboxyaryl groups, carboxyalkylaryl groups, carboxyarylalkyl group, and carboxyalkylarylalkyl groups. Examples and definitions of the hydrocarbyl groups to which the carboxy group is bound are also given below in the context of the hydrophobic substituents. Multiple different such hydrocarbyl groups may be combined. However, the log P values and/or the carbon atom number definitions given above apply.

It is possible to replace 1, 2 or 3, preferably 1 or 2, of the carbon atoms of the hydrocarbyl moieties of the carboxylated substituents by oxygen, nitrogen or sulfur, thereby forming carboxyheterohydrocarbyl moieties. It is understood that any such formal replacement by a heteroatom will include adjustment of bound hydrogen atoms to adjust to the valency of the exchanged heteroatom. In preferred embodiments, such carboxyheterohydrocarbyl moieties comprise one or more functional group selected from —O—, —S—, —N(H)C(O)—, —C(O)O—, —OC(O)N(H)—, —C(O)—, —C(O)—N(H)—, —N(H)—C(O)—O—, —O—C(O)—, or —S—S— in the hydrophobic linker.

In one aspect of the invention, the hydrophobic linkers are or comprise alkylene groups such as linear or branched alkylene groups, or the linkers are or comprise cycloalkylene groups. Alkylene groups may be n-alkylene or isoalkylene groups. Examples of alkylene groups are propylene, butylene, pentylene, hexylene, heptylene, octylene, nonylene, decylene, undecylene, dodecylene, tetradecylene or hexadecylene groups. Examples of cycloalkylene groups are cyclopentylene, cyclohexylene and cycloheptylene groups. Examples of alkylcycloalkyl groups are methylcyclopentylene, ethylcyclopentylene, propylcyclopentylene, butylcyclopentylene, pentylcyclopentylene, hexylcylopentylene, methylcyclohexylene, ethylcyclohexylene, propylcyclohexylene, butylcyclohexylene, pentylcyclohexylene and hexylcylohexylene. One or more of these may be combined in a hydrophobic linker.

The carboxylated substituents may be or may comprise carboxyalkyl or carboxycycloalkyl groups and comprise from 6 to 20. Such carboxylated substituents may be selected from the group consisting of carboxy-n-alkyl groups, branched carboxyalkyl groups or cyclic carboxyalkyl groups and their constitution or conformation isomers. In a preferred embodiment, the carboxyalkyl groups are radicals of acids selected from hexanoic acid, heptanoic acid, octanoic acid, nonanoic acid, decanoic acid, undecanoic acid, dodecanoic acid, tetradecanoic acid, hexadecanoic acid, 2-cyclohexylacetic acid, 4-cyclohexylbutyric acid, 6-cyclohexylhexanoic acid, 2-(2', 3' or 4' ethylcyclohexyl)-acetic acid or 4-(2', 3' or 4' ethylcyclohexyl)-butyric acid or 6-(2', 3' or 4' ethylcyclohexyl)-hexanoic acid.

In another aspect of the invention, the hydrophobic linkers are or comprise arylene groups and have from 6 to 20 carbon atoms. Aryl groups forming said arylene groups include aromatic hydrocarbyl groups (carbon-only aryl groups) and aromatic heterohydrocarbyl groups (heteroaryl groups). Examples of the former are phenyl, naphthyl, anthracenyl and phenanthryl. Nitrogen-containing heteroaryl groups preferably shall have a pK value of <5 for avoiding additional cationic charges at neutral pH. Examples of such nitrogen-containing heteroaryl groups are indolyl groups pyrazinyl groups, pyridazinyl groups, pyrimidinyl groups, cinnolinyl groups, phthalazinyl groups and purinyl groups. Oxygen-containing heterohydrocarbyl groups that form hydroxy groups preferably have a pK>12 for avoiding negative charges at neutral pH.

Examples of alkylaryl groups are methylphenyl (tolyl), ethyiphenyl, 4-isopropylphenyl, and xylyl groups. Examples of arylalkyl (aralkyl) groups are benzyl, phenylethyl and trityl groups. Examples of alkylarylalkyl groups are methylbenzyl and 4-isopropylbenzyl groups.

Carboxyarylalkyl moieties may for example be radicals derived from o, m or p-methyl benzoic acid, or o-, m- or p-ethyl benzoic acid. Carboxyalkylarylalkyl moieties may for example be o-, m- or p-methyl phenylacetic acid. Carboxyalkenylarylalkyl moieties may for example be or from o-, m- or p-methyl cinnamic acid.

Multiple carboxylated substituents such as those being or comprising carboxyalkyl groups present on the polyamine derivative of the invention may be the same or different. For simplicity, they may be the same. The carboxy group of the carboxylated substituent may be bound to any carbon atom of the hydrophobic linker. Preferably, the carboxy group is bound to a carbon atom as follows: if z is the number of carbon atoms in the longest carbon chain in the carboxylated substituent (such as the carboxyalkyl group) to the carbon atom that is bound to a polyamine nitrogen atom, the carboxy group is bound to a carbon atom at a position that is more than z/2 atom positions away from the polyamine nitrogen, if the carbon atom bound to the polyamine nitrogen is counted as position 1. If the value of z/2 is not an integer, the above definition leads to the position defined by the next integer >z/2. In one embodiment, the carboxy group is bound to the carbon atom of the hydrophobic linker that is most remote (in terms of the number of carbon atoms) from the polyamine nitrogen atom to which the hydrophobic linker (alkylene chain in the case of carboxyalkyl groups) is connected. The carboxy group may be bound to the carbon atom that is farthest away from the polyamine nitrogen within the carboxylated substituent (or carboxyalkyl group), such as to the terminal (omega position) carbon atom of the carboxylated substituents (or carboxyalkyl group) in case of a linear carboxylated substituent.

The possible groups given above for the hydrophobic linkers may be substituted provided the log P values given above are fulfilled. Alternatively, the possible groups given above for the hydrophobic linkers may be substituted provided the carbon atom numbers and numbers of possible heteroatoms as defined above are fulfilled.

Hydrophobic Substituents

The hydrophobic substituents may be bonded to amino groups of the polyamine and may have a log P of from 1.5 to 20, preferably of from 2 to 15, more preferably of from 2.5 to 10, determined for a compound obtainable from said hydrophobic substituent by replacing its bond to an amino group of the polyamine by a bond to a hydrogen atom. Methods to determine the log P are known to the skilled artisan and comprise the experimental determination of the compound distribution between water and 1-octanol, or obtaining such values from reference sources such as Wikipedia, the English version, or calculating the log P using software such as ACD/Labs 7.0 (Advanced Chemistry Development, Ontario, Canada).

The hydrophobic substituents comprise from 2 to 40 carbon atoms, in some aspects from 3 to 40 carbon atoms, in preferred aspects from 6 to 40 carbon atoms and in more preferred aspects from 6 to 20 carbon atoms. The hydrophobic substituents may comprise from 1 to 3, preferably 1 or 2, heteroatoms selected from O, N, and S, provided said hydrophobic substituents comprise 6 or more carbon atoms.

Preferably, the heteroatoms are selected from O and S. Thus, the hydrophobic substituents may be hydrocarbyl groups or heterohydrocarbyl groups, the latter comprising from 1 to 3 heteroatoms as mentioned before. Among the plurality of hydrophobic substituents of a molecule of said polyamine derivative, there may be exclusively hydrocarbyl groups, exclusively heterohydrocarbyl groups, or there may be hydrocarbyl groups and heterohydrocarbyl groups. In one embodiment, the plurality of hydrophobic substituents are all hydrocarbyl groups. In another embodiment, the plurality of hydrophobic substituents are all heterohydrocarbyl groups.

Where the hydrophobic substituents are hydrocarbyl groups, they may be selected from alkyl groups, alkenyl groups, alkynyl groups, cycloalkyl groups, cycloalkenyl groups, cycloalkylalkyl groups, alkylcycloalkyl groups, alkylcycloalkylalkyl groups, aryl groups, alkylaryl groups, arylalkyl groups, and alkylarylalkyl groups and groups comprising two or more groups from the aforementioned list. Provided the hydrophobic substituent comprises 6 or more carbon atoms, it is possible to replace 1, 2 or 3 of the carbon atoms of said hydrocarbyl groups by oxygen, nitrogen or sulfur, preferably oxygen or sulfur, thereby forming heterohydrocarbyl substituents. Such heterohydrocarbyl substituents may comprise functional groups selected from —O—, —S—, —N(H)C(O)—, —C(O)O—, —OC(O)N(H)—, —C(O)—, —C(O)—N(H)—, —N(H)—C(O)—O—, —O—C(O)—, or —S—S—.

In one aspect of the invention, the hydrophobic substituents are or comprise alkyl groups such as linear or branched alkyl groups, or cycloalkyl groups. Alkyl groups may be n-alkyl or isoalkyl groups. Examples of alkyl groups are propyl, butyl, pentyl, hexyl, heptyl, octyl, nonyl, decyl, undecyl, dodecyl, tetradecyl or hexadecyl groups. Examples of cycloalkyl groups are cyclopentyl, cyclohexyl and cycloheptyl groups.

Examples of alkenyl groups are propenyl, butenyl, pentenyl, hexenyl, heptenyl, octenyl, nonenyl, decenyl, undecenyl, dodecenyl, tetradecenyl and hexadecenyl groups. Examples of alkynyl groups are propynyl, butynyl, pentynyl, hexynyl, heptynyl, octynyl, nonynyl, decynyl, undecynyl, dodecynyl, tetradecynyl and hexadecynyl groups.

Examples of cycloalkenyl groups cyclopentenyl, cyclohexenyl and cycloheptenyl groups.

Cycloalkylalkyl groups are groups wherein a cycloalkyl group is linked to an alkylene group corresponding to an alkyl group. Examples are cyclopentylmethyl, cyclopentylethyl, cyclohexylmethyl, cyclohexylethyl etc.

Alkylcycloalkyl groups are groups wherein an alkyl group is linked to a cycloalkylene group corresponding to a cycloalkyl group. Examples of alkylcycloalkyl groups are methylcyclopentyl, ethylcyclopentyl, propylcyclopentyl, butylcyclopentyl, pentylcyclopentyl, hexylcyclopentyl, methylcyclohexyl, ethylcyclohexyl, propylcyclohexyl, butylcyclohexyl, pentylcyclohexyl and hexylcylohexyl.

Alkylcycloalkylalkyl groups are groups wherein an alkyl group is linked to a cycloalkylalkylene group.

In another aspect of the invention, the hydrophobic substituent comprises an aryl groups and has from 6 to 20, preferably from 7 to 15 carbon atoms. Aryl groups include aromatic hydrocarbyl groups (carbon-only aryl groups) and aromatic heterohydrocarbyl groups (heteroaryl groups). Examples of the former are phenyl, naphthyl and phenanthryl. Nitrogen-containing heteroaryl groups preferably have a pK value of <5 for avoiding additional cationic charges at neutral pH. Examples of such nitrogen-containing heteroaryl groups are indolyl groups pyrazinyl groups, pyridazinyl groups, pyrimidinyl groups, cinnolinyl groups, phthalazinyl groups and purinyl groups. Oxygen-containing heterohydrocarbyl groups that form hydroxy groups preferably have a pK>12 for avoiding negative charges at neutral pH.

Examples of alkylaryl groups are methylphenyl (tolyl), ethylphenyl, 4-isopropylphenyl, methylindolyl and xylyl groups. Examples of arylalkyl (aralkyl) groups are benzyl, phenylethyl, indolylmethyl and trityl groups. Examples of alkylarylalkyl groups are methylbenzyl and 4-isopropylbenzyl groups.

Different hydrophobic substituents on a molecule of the polyamine derivative may be the same or may be different. For simplicity, they may be the same.

The possible groups given above for the hydrophobic substituents may be substituted provided the carbon atom numbers and numbers of possible heteroatoms as defined above are fulfilled for the substituted hydrophobic substituent.

Preferred Polyamine Derivatives

The polyamine derivative of the invention may be a linear polyalkylenimine derivative comprising units of the following formula (10):

$$-[CH_2-NR^{10}-(CH_2)_x]- \qquad (10)$$

wherein
x is an integer of from 1 to 10, wherein the value of x may be the same or different among different groups $(CH_2)_x$,
$R_{10}$ is hydrogen,
the carboxylated substitutent comprising a carboxyl group bonded via a hydrophobic linker (as defined above) to the amino nitrogen to which $R^{10}$ is bonded, or
the hydrophobic substituent as defined above,
each of which is present in a molecule of said polyalkylenimine among different occurrences of $R^{10}$.

The number of nitrogen atoms per molecule of said linear polyalkylenimine or another polyamine moiety of the polyamine derivative may be from 12 to 100000, preferably from 12 to 20000, more preferably from 20 to 10000, and most preferably of from 20 to 5000. Multiple occurrences of $R^{10}$ may be the same of different.

The linear polyamine derivative that was defined above by way of the repeating units of the polymer chain has terminal groups that are generally as formed in the production of the underlying polyamine. Thus, there are no limitations in the invention regarding the end groups. In the case of linear polyethylenimines, there may be hydroxyethyl end groups. Examples for end groups are those of $R^8$ defined below.

Alternatively, the polyamine derivative of the invention is a branched polyalkylenimine derivative comprising units of each of the formulae (11), (12) and (13):

$$-[CH_2-NR^{10}-(CH_2)_x]- \qquad (11)$$

$$-[CH_2-NR^{11}-(CH_2)_x]- \qquad (12) \text{ and}$$

$$-(CH_2)_y-NR^{10}_2 \qquad (13)$$

wherein
$R^{10}$ and x are as defined above;
$R_{11}$ comprises one or more units selected from formulae (11), (12) and (13);
y is an integer of from 1 to 10, wherein the value of y may be the same or different among different groups $(CH_2)_y$; and
wherein the number of nitrogen atoms per molecule of said linear or said branched polyalkylenimine is from 12 to 100000.

The number of nitrogen atoms per molecule of said branched polyalkylenimine may be as defined above for the linear polyalkylenimine. Examples for end groups are those of $R^8$ defined below. The degree of branching in the branched polyalkylenimine may be of from 1 to 40%, preferably from 10 to 40%, more preferably from 15 to 30%. The skilled artisan knows how to quantify the branching of a polymer, e.g. through pH-titrations and quantification of the different compartments of the titration curve or by 1H NMR analysis.

Combinations of carboxylated substituents and hydrophobic substituents in the polyamine derivatives can be characterized by their molar ratio. It was found that the polyamine derivatives (such as polyethylenimine derivatives) of the invention perform best if the carboxylated substituents and hydrophobic substituents have a molar ratio of from 10:1 to 0.1:1 (the C/A ratio). In a preferred embodiment, the C/A ratio of these groups is from 3:1 to 0.33:1.

When grafted onto a polyamine, the degree of substitution (DOS) is another feature of relevance. The DOS is defined as the molar percentage of the sum of carboxylated substituents and hydrophobic substituents per amino group of the polyamine. The DOS is least 10%, preferably from 25 to 80%, more preferably from 30 to 60%. A person skilled in the art knows how to determine the DOS of a polyamine derivative. This can be achieved by measurement of the residual nitrogen atoms on a polymer for example using the ninhydrin reaction. Another possibility is the use of 1H-NMR spectroscopy.

In some aspects, the invention is practiced with a combination of one specific type of carboxylated substituents and one specific type of hydrophobic substituents per molecule of polyamine derivative. In such aspects, the sum of carbon atoms of one carboxylated substituent plus that in one hydrophobic substituent is from 10 to 30, preferably this sum is from 15 to 25.

In further aspects, specific combinations are made between a polyamine type, polyamine molecular mass, size of the carboxylated substituents and size of the hydrophobic substituents. In one preferred embodiment of such aspect, the polyamine derivative has a linear polyethylenimine moiety of from 2 to 500 kDa (in terms of number average molecular weight), the carboxylated substituents have from 11 to 16 carbon atoms and are n-alkylcarboxylic acids and the hydrophobic substituents have from 3 to 12 carbon atoms and are alkyls, preferably n-alkyls, or alkylcyclohexyls.

In other preferred embodiments, the polyamine derivative has a branched polyethylenimine moiety of from 0.5 to 200 kDa (in terms of number average molecular weight), the carboxylated substituents have from 11 to 16 carbon atoms and are n-alkylcarboxylic acids and the hydrophobic substituents have from 6 to 12 carbon atoms and are alkyls, preferably n-alkyls, or alkylcyclohexyls.

In further preferred embodiments, the polyamine derivative has a linear polyethylenimine moiety of from 2 to 500 kDa (in terms of number average molecular weight), the carboxylated substituents have from 11 to 16 carbon atoms and are n-alkylcarboxylic acids and the hydrophobic substituents have from 6 to 12 carbon atoms and are aryls, preferably selected from aryls comprising a benzyl, isopropylbenzyl, naphtyl or indolyl moiety.

In other preferred embodiments, the polyamine derivative has a branched polyethylenimine moiety of from 0.5 to 200 kDa (in terms of number average molecular weight), the carboxylated substituents have from 11 to 16 carbon atoms and are n-alkylcarboxylic acid groups, and the hydrophobic substituents have from 6 to 12 carbon atoms and are aryl-containing groups, preferably selected from groups comprising a benzyl, isopropylbenzyl, napthyl or indolyl moiety.

In yet other preferred embodiments, the polyamine derivative has a linear oligospermine or oligosperminhomologue moiety of from 1 to 10 kDa (in terms of number average molecular weight), the carboxylated substituents have from 11 to 16 carbon atoms and are n-alkylcarboxylic acid groups, and the hydrophobic substituents have from 4 to 10 carbon atoms and are alkyls, preferably n-alkyl groups.

In one embodiment, the polyamine derivative of the invention is a carboxyalkyl-alkyl polyamine. The alkyl moieties comprise at least 2 carbon atoms. In some aspects of the invention, the alkyl moieties have from 3 to 40 carbon atoms. In preferred aspects, the alkyl moieties are linear alkyl groups having from 6 to 40 carbon atoms, in more preferred aspects the number of carbon atoms is from 6 to 20. Multiple alkyl groups present on a polyamine may be the same or different. In other aspects of the invention, the alkyl moieties also comprise aromatic rings and have from 6 to 40 carbon atoms.

Carboxyalkyl-alkyl-polyamine

The carboxyalkyl-alkyl-polyamine may be a linear carboxyalkyl-alkyl-polyalkylenimine comprising, or consisting essentially of, units of the formula (6):

—[CH$_2$—NR$^6$—(CH$_2$)$_x$]—  (6), wherein x is an integer of from 1 to 10, and wherein the value of x may be the same or different among different groups (CH$_2$)$_x$; R$^6$ is hydrogen, an alkyl group of formula C$_r$H$_{2r+1}$ or a carboxyalkyl group of formula C$_{s-1}$H$_{2s-2}$COOH. Each of these groups of R$^6$ is present in a molecule of said carboxyalkyl-alkyl-polyamine among different occurrences of R$^6$; r is an integer of from 2 to 40, and s is an integer of from 4 to 40. Preferred embodiments for x are as defined above in the context of formula (1). Numeral r is preferably of from 6 to 40, more preferably from 6 to 20. Numeral s is preferably from 4 to 20, more preferably from 6 to 20, and even more preferably from 8 to 16.

The number of nitrogen atoms per molecule of said linear carboxyalkyl-alkyl-polyalkylenimine may be from 12 to 100000, preferably from 12 to 20000, more preferably from 20 to 10000, and most preferably of from 20 to 5000.

The linear carboxyalkyl-alkyl-polyamine that was defined above by way of the repeating units of the polymer chain has terminal groups that are generally as formed in the production of the underlying polyamine. Thus, there are no limitations in the invention regarding the end groups. Examples for end groups are those of $R^8$ defined below.

Alternatively, said carboxyalkyl-alkyl-polyamine is a branched carboxyalkyl-alkyl-polyalkylenimine. The branched carboxyalkyl-alkyl-polyalkylenimine may be one comprising structural units of each of the formulae (7), (8) and (9):

—[CH$_2$—NR$^6$—(CH$_2$)$_x$]—  (7)

—[CH$_2$—NR$^7$—(CH$_2$)$_x$]—  (8)

—(CH)$_y$—NR$^6_2$  (9)

wherein
R$^6$, x, r and s are as defined above;
R$^7$ comprises one or more structures selected from formulae (7), (8) and (9);

y is an integer of from 1 to 10, preferably of from 2 to 10, more preferably of from 2 to 6, wherein the value of y may be the same or different among different occurrences of groups $(CH_2)_y$.

$R^7$ may be a group of formula (9) or $R^7$ comprises one or more units of formula (7) and/or (8). It is also possible that $R^7$ comprises one or more units of formula (7) and one or more units of formula (8). As the carboxyalkyl-alkyl-polyalkylenimine is polymeric, one molecule thereof generally comprises multiple groups $R^7$ that differ in structure.

The number of nitrogen atoms per molecule of said branched carboxyalkyl-alkyl-polyalkylenimine may be from 12 to 100000, preferably from 20 to 20000, more preferably from 20 to 10000, and most preferably of from 20 to 5000.

The degree of branching in the branched polyalkylenimine may be of from 1 to 40%, preferably from 10 to 40%, more preferably from 15 to 30%. The skilled artisan knows how to quantify the branching of a polymer, e.g. through pH-titrations and quantification of the different compartments of the titration curve.

Molar ratios of carboxyalkyl and alkyl groups in the above-described carboxyalkyl-alkyl-polyalkylenimine may be as defined below. The degree of substitution (DOS) may also be as defined below.

In some aspects, the invention using a carboxyalkyl-alkyl-polyalkylenimine is practiced with specific combinations of carboxyalkyl and alkyl moieties. In preferred embodiments, a carboxyalkyl group is combined with an aliphatic alkyl group and the sum of carbon atoms in both moieties is between 10 and 30, in more preferred embodiments this sum is between 15 and 25. In these embodiments, one type of carboxyalkyl group is preferably combined with one type of alkyl group.

In further aspects, specific combinations are made between a polyamine type, polyamine molecular mass, length of the carboxyalkyl groups and lengths of the alkyl groups. In one preferred embodiment of such aspect, the polyamine is a linear polyethylenimine of between 2 and 30 kDa (in terms of number average molecular weight), the carboxyalkyl group has from 8 to 16 carbon atoms and the alkyl has from 6 to 16 carbon atoms. Even more preferred are combinations wherein the carboxyalkyl group has from 10 to 16 carbon atoms and the alkyl has about 9 carbon atoms. In another preferred embodiment, the polyethylenimine is a branched polymer of about 10 kDa and the carboxyalkyl group has between 8 and 16 carbon atoms and the alkyl has between 6 and 16 carbon atoms, more preferably about 9 carbon atoms.

Combinations of carboxyalkyl and alkyl groups in the carboxyalkyl-alkyl-polyamine can be characterized by their molar ratio. It was found that the carboxyalkyl-alkyl-polyamines (such as the carboxyalkyl-alkyl-polyethylenimines) of the invention perform best if the carboxyalkyl and alkyl moieties have a molar ratio of from 6:1 to 0.33:1 (the C/A ratio). In a preferred embodiment, the C/A ratio of these groups is between 3:1 and 0.8:1. In a more preferred embodiment, the polyamine is a polyethylenimine that is substituted with a C11 carboxyalkyl group and a C9 alkyl group, wherein the C/A ratio is from 2:1 to 0.5:1, more preferably about 1.

When grafted onto a polymer, the degree of substitution (DOS) is another feature of relevance. The DOS is defined as the molar percentage of the sum of carboxyalkyl moieties and alkyl moieties per amino group of the polyamine. The DOS is least 10%, preferably between 25 and 80%, more preferably between 30 and 60%. A person skilled in the art knows how to determine the DOS of a polyamine derivative. This can be achieved by measurement of the residual nitrogen atoms on a polymer for example using the ninhydrin reaction. Another possibility is the use of 1H-NMR spectroscopy.

In a particularly preferred example, the polyamine is a polyethylenimine that is substituted with a C11 carboxylic acid and a C9 alkyl group, wherein the C/A ratio is from 2:1 to 0.5:1, and the DOS is between 35 and 45%.

The following table 3 lists some specific embodiments of polyamine derivatives. For a list of the abbreviations or symbolic names see examples 11 and 15.

TABLE 3

| polymer | Mr of the polyamine in kDa | carboxy moiety | hydrophobic moiety | C/A ratio | DOS |
|---|---|---|---|---|---|
| Polyamine derivatives for the transfection of small, double stranded RNA | | | | | |
| linear polyethylenimine | 2.5 kDa | C11 | nonyl | 0.8-4 | 40-60% |
| linear polyethylenimine | 25 kDa | C11 | nonyl | 1.5-4 | 50-70% |
| branched polyethylenimine | 10 kDa | C11 | nonyl | About 1 | 35-45% |
| branched polyethylenimine | 10 kDa | C11 | nonyl | 1.5-5 | 35-55% |
| linear polyethylenimine | 25 kDa | C16 | ethylcyclohexyl | 1.3-6 | 15-35% |
| linear polyethylenimine | 100 kDa | C16 | nonyl | 2.5-6 | 15-35% |
| branched polyethylenimine | 1.2 kDa | C16 | hexyl | 0.4-2.5 | 30-60% |
| branched polyethylenimine | 10 kDa | C11 | ethylcyclohexyl | 0.12-1 | 35-60% |
| branched polyethylenimine | 70 kDa | C16 | nonyl | 0.12-1 | 25-50% |
| branched polyethylenimine | 70 kDa | C16 | ethylcyclohexyl | 0.75-5 | 25-50% |
| branched polyethylenimine | 1.8 kDa | C16 | 4-isopropylphenylmethyl | 0.12-1.3 | 25-50% |
| branched polyethylenimine | 10 kDa | C16 | 4-isopropylphenylmethyl | 0.1-1.3 | 20-35% |

TABLE 3-continued

| polymer | Mr of the polyamine in kDa | carboxy moiety | hydrophobic moiety | C/A ratio | DOS |
|---|---|---|---|---|---|
| Polyamine derivatives for the transfection of DNA | | | | | |
| Linear polyethylenimine | 100 | C16 | propyl | 0.12-1 | 20-50% |
| Linear polyethylenimine | 250 | C16 | propyl | 0.12-1 | 20-50% |
| Branched polyethylenimine | 1.2 | C11 | dodecyl | 0.3-1.3 | 30-55% |
| Branched polyethylenimine | 1.8 | C11 | dodecyl | 0.3-1.3 | 30-55% |
| Branched polyethylenimine | 1.8 | C16 | benzyl | 0.4-1.3 | 30-50% |
| Linear polyethylenimine | 25 | p-ethyl-benzoic acid | nonyl | 0.75-3 | 20-50% |
| Polyamine derivatives based on oligospermines | | | | | |
| X = 2, 4 or 2, 5 | 1-4 kDa | C11 ... C16 | Butyl | 0.2-1 | 50-100% |
| X = 2, 3 or 2, 4 or 2, 5 | 1-6 kDa | C11 ... C16 | Hexyl | 0.2-1 | 50-100% |
| X = 2, 3 | 2-6 kDa | C11 | Decyl | 0.2-1 | 50-100% |

Throughout this description, structural formulae are given in the uncharged or non-ionised form. It is, however, clear to the skilled person that nitrogen atoms of these structures may be protonated, notably in aqueous solutions. Thus, compounds defined by way of any of these formulae also comprise the compounds or ions wherein any one of the nitrogen atoms is in a charged state.

Manufacture of Polyamine Derivatives

The polyamine derivatives of the invention may be prepared by modification of any of the polyamines described above with the carboxylated substituents and hydrophobic substituents described above. Such methods are well known in the art and are further illustrated in the examples. For example, the carboxylated substituents and the hydrophobic substituents are introduced via their corresponding halogenated compounds by derivatizing the polyamine under alkaline conditions with a halogenated carboxylic acids and a halogenated hydrophobic compound. Bromine is preferred as the halo atom in these compounds. In a preferred embodiment, this is achieved by the use of α,ω-bromocarboxylic acid and bromo compounds such as bromoalkanes or bromoaryls as the halo compounds. These two derivatizations may be done consecutively or in parallel using a mixture of the halogenated carboxylic acid and the halogenated hydrophobic compound. The mixing ratio of the halogenated carboxylic acid and the halogenated hydrophobic compound are suitably chosen for achieving the desired molar ratio of carboxyl and the hydrophobic groups in the polyamine derivative to be prepared. In an approximation, the molar mixing ratio of the halogenated carboxylic acid and the halogenated hydrophobic compound in the parallel modification reaction corresponds to the molar ratio of carboxylated substituents and hydrophobic substituents in the polyamine derivative. The molar ratio of carboxylated substituents and the hydrophobic moieties in the product obtained may be analysed e.g. by 1H-NMR. Deviations in the found molar ratio from the desired molar ratio may be used to adjust the mixing ratio of the halogenated carboxylic acid and the halogenated hydrophobic compound in order to obtain a modified polyamine substituted with the desired molar ratio these substituents. It is clear to the skilled person that the desired degree of substitution (DOS) can be achieved and, if necessary, adjusted in a similar way by using suitable relative molar amounts of the halogenated carboxylic acid and the halogenated hydrophobic compound on the one hand to the amount of polyamine on the other hand. The reaction is generally carried out in an organic solvent, preferably a polar organic solvent such as alcohols. In other embodiments, the introduction of the carboxylated substituents and hydrophobic substituents is achieved through acylation using the corresponding dicarboxylic acids, their anhydrides or chlorides, or through Michael-addition using the respective unsaturated derivatives of the carboxylic acid and the halogenated hydrophobic compound.

The polyamine derivatives of the present invention are different from the compounds described in the state of the art. Wakefield et al. (2005) Bioconj Chem 16(5):1204-1208 report on copolymers from aminoethyl-vinylether and alkyl-vinylethers having alkyl groups with one to four carbon atoms. In contrast to the present invention, the polymers of Wakefield do not comprise carboxyl moieties, they are thus missing an essential type of a functional group on the polymer. The polyamine derivatives of the present invention are also different from the modified polyethylenimines presented by van Vliet et al. (2008) in Chembiochem, 2008, 9, 1960-1967. There, polyethylenimines were systematically modified with dodecyl, benzyl and methyl moieties. Again, the essential carboxyalkyl groups of the present invention are not used in van Vliet. In addition, extensive formation of quaternized amino groups occurs through the use of methyl iodide.

In contrast to Wakefield or van Vliet, the WO08/074488 and Oskuee et al. (2010) J Gene Med 12:729-738 are both silent on the use of additional alkyl groups. In fact, the WO08/074488 clearly differentiates between the use of carboxyalkyl groups (the TEE's therein) and the merely hydrophobic modifications achieved by alkylation (page 60 of the A2 document). Oskuee, on the other hand, teaches that the effect of carboxylation is mediated through reduced surface charge, a feature not mediated through alkylation.

Use of the Polyamine Derivatives of the Invention as Transfectants

The polyamine derivative of the invention such as the carboxyalkyl-alkyl-polyamine is used for the transfection of polyanions into cells. Therefore, these polyamine derivatives are also referred to herein as transfectants of the invention.

The polyanions can be selected from the group of peptides, proteins and nucleic acids. In certain embodiments the polyanions are proteins selected from antibodies. In specific embodiments the antibodies are of IgG type. In other embodiments antibody fragments are used, such as Fab, Fab', disulfide-linked F(ab')2 fragments or chemically linked F(ab')2 fragments or scFv fragments. In a preferred embodiment, the polyanions are nucleic acids.

Nucleic acids as used herein are polynucleotides or oligonucleotides, including, without limitation, DNA or RNA or derivatives or analogs thereof. Polynucleotide as used herein refers to any polyribonucleotide or polydeoxyribonucleotide, which may be of unmodified RNA or DNA or of modified RNA or DNA or of mixed DNA/RNA. Polynucleotides can be single or double stranded. A plasmid is an example for a double stranded polynucleotide, a mRNA is an example for a single stranded polynucleotide. Oligonucleotides as used herein are defined as molecules with two or more nucleotides, often more than three, and usually more than ten and less than a hundred which may be of unmodified RNA or DNA or of mixed DNA/RNA or of modified RNA or DNA, wherein the modifications include ring bridging such as found in LNA (locked nucleic acids), various modifications in the 2' position of the nucleoside such as 2'Me, 2'OMe, 2'MOE, 2'F and the like or wherein sugars other than ribose are used, such as arabinose in the 2'FANA nucleotides, glycerols in the unlocked nucleic acids or hexitol structures. The size of an oligonucleotide may depend on many factors, including the ultimate use of the oligonucleotide. Typical examples for oligonucleotides are siRNA, antisense inhibitors, miRNA, DNAzymes, aptamers and the like. Essentially, all nucleic acids carrying negative charges on their backbone are compatible for use with the transfectants of the invention, this includes various backbone-modified nucleic acids such those comprising phosphothioate linkages or phosphodithionate linkages. In contrast, uncharged nucleic acids such as those built from methylphosphonates or peptide-nucleic acids (PNA's) are less compatible with the transfectants of the invention.

For transfecting a nucleic acid or other polyanion, a complex between the nucleic acid (or other polyanion) and the transfectant is generally made. The formation of complexes between transfection reagents and polyanions is known to the person skilled in the art. Generally, this may be achieved by combining a first solution comprising the transfectant and a second solution comprising the polyanion or nucleic acid. Typically, the number of cationic charges provided by the transfectant is higher than the number of negative charges on the polyanion. This ratio is known as an N/P ratio in the art, wherein N denotes the number of the formal nitrogen charges on the transfectant and P the number of phosphate groups on a nucleic acid. In some embodiments the N/P ratio for the use of the polyamine derivative in combination with nucleic acids is between 2 and 20, in preferred embodiments such ratio is between 5 and 15 and in even more preferred embodiments the N/P ratio is about 10.

In other embodiments, the N/P ratio is between 2 and 6, more preferred around 4. Depending on the N/P ratio, the complexes between a nucleic acid and a polyamine derivative may have different charges and a different particles size. Complexes having a N/P value of about 10 or more have a neutral or slightly positive surface charge as determined by zeta potential measurements. The particle size of such complexes is between 200 and 1000 nm, in preferred embodiments between 250 and 500 nm as determined by dynamic light scattering.

Complexes having a N/P of about 6 or lower have a neutral to negative surface charge as determined by zeta potential measurements. The particle size of complexes having a N/P of about 6 or smaller is between 50 and 500 nm, in preferred embodiments between 100 and 200 nm as determined by dynamic light scattering.

It is well known to the person skilled in the art that the particle size and surface charge of a particle are determinants for the distribution of particles in the systemic circulation of a vertebrate animal, a mammal or in humans. Particles having a size of 150 nm or below are able to reach the liver parenchyma from the blood stream while large particles are excluded. In contrast, tumors, sites of inflammation or the stroma cells in the spleen can be reached by larger particles up to about 500 nm.

Complex formation between the transfectant of the invention and the polyanion to be transfected is generally carried out. Complex formation between the polyanions such as nucleic acid involves a charge interaction with the transfectant. Such interaction is achieved in aqueous solution in a pH range between 3 and 9 where both complex partners are ionized. In some embodiments the pH for complex formation is between 4 and 8 and in preferred embodiments said pH is between 5 and 7. The pH of the complex forming solution is adjusted by the use of one or more buffer substances. In principle, any buffer substance having a pK within the aforementioned range and being non-toxic to cells can be used. In preferred embodiments, buffers based on acetate, maleate, succinate, carbonates, phosphates, citrate, methylethylsulfonate (MES), Bis-Tris, Bis-Tris-propane, tris-(hydroxymethyl)aminomethan, tricine or buffers of the Good series such as HEPES, TES, MOPS, BES, MOPSO, ACES, PIPES, ADA, HEPPS are used. More preferred buffers are acetate, phosphates, citrate or HEPES.

The solution wherein the complex formation occurs may comprise other ingredients such as salts or sugars as long as these substances do not compete with the complex formation or are toxic to the cells. In preferred embodiments, the amount of salts is limited so that the total ionic strength of the solution is below 0.2 mol/L, in more preferred embodiments the ionic strength is below 0.1 mol/L. A salt well tolerated by cells is sodium chloride. A low ionic strength below 0.1 mol/L is preferred for the binding of oligonucleotides whereas for the complex formation with polynucleotides such as plasmids or mRNA the ionic strength may be higher.

To avoid osmotic stress during the addition of the transfection complex to cells, sugars can be added to the complex forming solution to adjust the osmolarity. In some embodiments the addition of sugars is limited so that the total osmolarity of the solution added to the cells is between 150 and 500 mosm/L, in preferred embodiments the osmolarity is between 270 and 310 mosm/L. In preferred embodiments, glucose, sucrose or trehalose are used to adjust the osmolarity of the transfection mixture.

It was surprisingly found that the transfection mixture can also be prepared using certain media with unknown composition. In many cases, the transfection mixture could be prepared with cell culture media, such as DMEM, Optimem (trademark of Life Technologies) and the like.

The transfectants of the present invention may have a limited solubility in water or buffered solutions. The solubility is a function of the pH and the accompanying ionization of the polyamine derivative of the invention. As a general rule, these compounds have a better solubility in water upon acidification, e.g. in media having a pH of 7 or less. On the contrary, the polyamine derivatives are easily soluble in alcohols as for example ethanol, propanol, 1,2-dihydroxypropane or isopropanol (that are also referred to herein collectively as "short-chain alcohol") at pH of 9 or higher. Depending on the pH, it is also possible to employ mixtures of short-chain alcohols with water as a solvent, for example mixtures having between 33 and 100% of ethanol, propanol, 1,2-dihydroxypropane or isopropanol for less ionized forms of the transfectants or mixtures having between 0 and 66% of said alcohols for more ionized forms of the transfectants. In certain embodiments, the transfectants are stored as stock solutions containing between 20 and 200 mM (based nitrogen atoms in the transfectant) of the transfectant in lower alcohols such as short-chain alcohols. Working concentrations of about 0.1 mM to 5 mM of the transfectant may then be generated by dilution of the stock into an aqueous buffer solution. Typically, the short chain alcohols need not be removed from the transfection mixture and are tolerated by the cells.

In a specific embodiment, the transfectants are used under the following transfection protocol:
1) Polyamine derivative is supplied as 50 mM solution (based on nitrogen content) in 33 to 100% ethanol, preferably 70° A) ethanol.
2) Transfection buffer comprising 10 mM sodium dihydrogenphosphate and 3 mM sodium hydroxide is prepared.
3) The modified polyamine is diluted in transfection buffer to a 1 mM solution.
4) siRNA is diluted in transfection buffer to 22 µM siRNA. Since the average number of phosphates on siRNA is about 45, the total concentration of phosphorus is about 1 mM
5) The working solutions of the polyamine and siRNA are combined in a 10+1 ratio which results in an N/P ratio of 10 and a concentration of the siRNA in the complexation mixture of 2 µM.
6) Up to 20 µl of the transfection mixture prepared in (5) is added per 100 µl of medium of cultivated cells.

In an alternative embodiment, the transfectants are used with the following general protocol:
1) Polyamine derivative is supplied as 50 mM solution (based on monomer weight) in 33 to 100%, preferably 70% ethanol.
2) Transfection buffer comprising 10 mM citric acid and 19 mM sodium hydroxide is prepared.
3) The modified polyamine is diluted in transfection buffer to a 1.8 mM solution.
4) siRNA is diluted in transfection buffer to 4 µM siRNA.
5) The working solutions of the polyamine and siRNA are combined in a 1+1 ratio which results in an N/P ratio of about 10 and a concentration of the siRNA during complexation of 2 µM.
6) Up to 20 µl of the transfection mixture prepared in (5) is added per 100 µl of medium of cultivated cells.

Transfectants having a small particle size can be prepared using the following general protocol 3:
1) Polyamine derivative is supplied as 56 mM solution (based on nitrogen content) in 33 to 100 ethanol, preferably 70% ethanol.
2) Transfection buffer comprising 10 mM sodium dihydrogenphosphate and 3 mM sodium hydroxide is prepared.
3) siRNA is diluted in transfection buffer to 18 µM siRNA. Since the average number of phosphates on siRNA is about 45, the total concentration of phosphorus is about 0.75 mM
4) The siRNA solution is added directly to the modified polyamine in a 20+1 ratio which results in an N/P ratio of 4 and a concentration of the siRNA in the complexation mixture of 17 µM.
5) Up to 10 µl of the transfection mixture is added per 100 µl of medium of cultivated cells or administered to animals.

While the preparation of transfection complexes from two solutions is often performed, it requires the separate preparation of the solutions containing transfectant and nucleic acid. The solutions need to be clean or sterile for their work in cell culture; they may also have a limited shelf life. A further improvement is the use of a dry transfectant that is reconstituted with transfection buffer before use. For this purpose, the transfectant can be dried down from its solution in short-chain alcohols. A particular benefit of such method is the provision of small and defined aliquots of transfectant having a very long shelf life. The dry transfectant can be rehydrated with transfection buffer. In some embodiments, the dry transfectant may also be rehydrated with a solution already containing the nucleic acid.

In other embodiments, the transfectant is provided in a lyophilized form. In a preferred aspect of such embodiment the transfectant is lyophilized from a solution comprising a buffer system adjusted to yield a pH between 5 and 7 and further comprising a sugar in an amount to yield a total osmolarity of between 100 and 500 mosm/L upon reconstitution, e.g. 270 mM sucrose or trehalose or glucose. In this embodiment, the nucleic acid is provided as a dilute aqueous solution and used directly for the reconstitution of the lyophilized transfectant, so that hydration and complex formation occur in a single step. The resultant transfection mixture can then directly be added to the cells to be transfected.

The transfectants of this invention can be marketed in the form of a kit, optionally further comprising a siRNA for control reactions.

In a first embodiment, the kit contains the following:
A) A solution of transfectant in a short-chain alcohol, wherein the alcohol may be 70% ethanol, and the transfectant may have a concentration of about 50 mM (based on nitrogen atoms in the transfectant),
B) A buffer solution having a pH between 4 and 8 and an ionic strength below 0.2, preferably below 0.1,
C) A manual with complete instructions, optionally also a short manual with condensed instructions.

In a second embodiment, such a kit comprises the following:
A) A solution of the transfectant as described in the first embodiment, wherein the solution is divided into aliquots. Preferentially, the number of aliquots is between 5 and 100, more preferred the number of aliquots is between 6 and 20. It is further preferred that each aliquot contains between 10 and 1000 nmol transfectant (based on monomer),
B) A buffer solution having a pH between 4 and 8 and an ionic strength below 0.2, preferably below 0.1,
C) A manual with complete instructions, optionally also a short manual with condensed instructions.

In a third embodiment, such kit comprises the following:
A) A solution of the transfectant as described in the first embodiment, wherein the solution is divided into aliquots and wherein such aliquots are arrayed in a microplate having between 6 and 1576 wells, preferably 24, 96 or 384 wells, and wherein each aliquot contains between 10 and 1000 nmol transfectant, B) A buffer solution having a pH between 4 and 8 and an ionic strength below 0.2, preferably below 0.1, C) A manual with complete instructions, optionally also a short manual with condensed instructions.

In a fourth embodiment, such a kit comprises the following:

A) A dry transfectant divided into aliquots. Preferentially, the number of aliquots is between 5 and 100, more preferred the number of aliquots is between 6 and 20. It is further preferred that each aliquot contains between 10 and 1000 nmol transfectant (based on monomer), B) A buffer solution having a pH between 4 and 8 and an ionic strength below 0.2, preferably below 0.1, C) A manual with complete instructions, optionally also a short manual with condensed instructions.

In a fifth embodiment, such a kit comprises the following:

A) A dry transfectant divided into aliquots, wherein such aliquots are arrayed in a microplate having between 6 and 1576 wells, preferably the microplate has 24, 96 or 384 wells, and wherein each aliquot contains between 10 and 1000 nmol transfectant, B) A buffer solution having a pH between 4 and 8 and an ionic strength below 0.2, preferably below 0.1, C) A manual with complete instructions, optionally also a short manual with condensed instructions.

In a sixth embodiment, such a kit comprises the following:

A) A lyophilized transfectant divided into aliquots. Preferentially, the number of aliquots is between 5 and 100, more preferred the number of aliquots is between 6 and 20. It is further preferred that each aliquot contains between 10 and 1000 nmol transfectant (based on monomer), B) A buffer solution having a pH between 4 and 8 and an ionic strength below 0.2, preferably below 0.1, C) A manual with complete instructions, optionally also a short manual with condensed instructions.

In a seventh embodiment, such kit comprises the following:

A) A lyophilized transfectant divided into aliquots, wherein such aliquots are arrayed in a microplate having between 6 and 1576 wells, preferably 24, 96 or 384 wells, and wherein each aliquot contains between 10 and 1000 nmol transfectant, B) A buffer solution having a pH between 4 and 8 and an ionic strength below 0.2, preferably below 0.1, C) a manual with complete instructions, optionally also a short manual ith condensed instructions.

In certain aspects of the third, fifth and seventh embodiment, all wells of such microplate contain the same amount of transfectant. In other aspects, the wells contain different amounts of transfectant. Such designs may involve gradients of the transfectants in neighboring wells which is useful during the optimization of N/P ratios with the nucleic acids. In yet other aspects, certain wells may be empty, e.g. for the generation of serial dilutions from a complexation mixture. FIGS. 1 to 4 further illustrate such designs of arrayed amounts of transfectants on the example of a 96 well plate.

In yet other embodiments the complexes of the polyamine derivative of this invention with one or more nucleic acids are formed and lyophilized and marketed as a complete product. This solution offers an even higher degree of integration compared to currently commercialized products. It also provides an opportunity to centralize the quality control of the product including its particle formation at the site of the manufacturer. Other advantages of the lyophilized complexes are their long storage stability and the absence of the short-chain alcohols used as solvent for the modified polyamines.

The lyophilized complexes between a polyamine derivative and one or more nucleic acids are of particular advantage for in vivo applications including animal research or for therapeutic use.

Lyophilized complexes can be manufactured with any of the general methods 1 to 3 described above with the inclusion of an lyophilization and rehydration step after the complexation.

In a specific embodiment, the complexes between the modified polyamines of the invention and one or more nucleic acids are prepared under the following protocol 4:

1) Modified polyamine is supplied as 50 mM solution (based on nitrogen content) in 33 to 100% ethanol
2) Transfection buffer comprising 10 mM sodium dihydrogenphosphate and 3 mM sodium hydroxide is prepared.
3) The modified polyamine is diluted in transfection buffer to a 1 mM solution.
4) siRNA is diluted in transfection buffer to 22 µM siRNA. Since the average number of phosphates on siRNA is about 45, the total concentration of phosphorus is about 1 mM
5) The working solutions of the polyamine and siRNA are combined in a 10+1 ratio which results in an N/P ratio of 10 and a concentration of the siRNA in the complexation mixture of 2 µM.
6) The complexes are optionally divided into aliquots, lyophilized, sealed with an air-tight seal and stored.
7) The lyophilized complexes are rehydrated with water.
8) Up to 20 µl of the rehydrated complex is added per 100 µl of medium of cultivated cells or the rehydrated complexes are administered to an animal or human being.

In a specific embodiment, the complexes between the modified polyamines of the invention and one or more nucleic acids are prepared under the following protocol 5:

1) Modified polyamine is supplied as 56 mM solution (based on nitrogen content) in 33 to 100% ethanol
2) Transfection buffer comprising 10 mM sodium dihydrogenphosphate and 3 mM sodium hydroxide is prepared.
3) siRNA is diluted in transfection buffer to 18 µM siRNA. Since the average number of phosphates on siRNA is about 45, the total concentration of phosphorus is about 0.75 mM
4) The siRNA solution is added directly to the modified polyamine in a 20+1 ratio which results in an N/P ratio of 4 and a concentration of the siRNA in the complexation mixture of 17 µM.
5) The complexes are optionally divided into aliquots, lyophilized, sealed with an air-tight seal and stored.
6) The lyophilized complexes are rehydrated with water
7) Up to 10 µl of the rehydrated complex is added per 100 µl of medium of cultivated cells or the rehydrated complexes are administered to an animal or a human being.

The administration of complexed nucleic acids to animals or human beings is known to persons skilled in the art and the complexed nucleic acids may be administered systemically or topically in doses required for the specific indication. The amounts of nucleic acid administered may vary between 0.1 µg and 100 mg per kg of body weight and can be administered once or multiple times or in complex or intermittent dosing regimens such a daily dosing, a dosing every other day or 3 times a week, once a week or once a month or a combination of such regimens.

DESCRIPTION OF THE FIGURES

FIGS. 1-4: The figures show various designs for transfectants arrayed in microplates. The numbers in the schematic microplates denote an amount of transfectant in nmol (based on nitrogen atoms) deposited in each well. The figures take 96 well plates as an example and place the transfectants in certain vertical rows. It is understood that similar designs can easily be derived from this general structure, e.g. where the patterns are organized horizontally, with more or less empty wells, with partial use of the plate and the like.

FIG. 1 Amount of transfectant in nmol placed into certain wells of a 96 well plate, even distribution.

FIG. 2 Amount of transfectant in nmol placed into certain wells of a 96 well plate, to simplify optimization of the N/P ratio.

FIG. 3 Amount of transfectant in nmol placed into certain wells of a microplate, including empty wells for serial dilutions of the transfection complexes.

FIG. 4 Amount of transfectant in nmol placed into certain wells of a microplate, facilitating a simple optimization of the N/P ratio and serial dilution of the transfection complexes.

EXAMPLES

The invention is now further illustrated with the following examples without being limited to these.

Example 1

Modification of Polyamines

Linear PEI (free base) having an average molecular mass of 2 kDa or 25 kDa was from Polysciences, catalog items 24313 and 23966, respectively. Branched PEI (free base) of 10 kDa size was from Aldrich, catalog item 408727. The polymers were dissolved in absolute ethanol at a concentration of 250 mono-mM; that is the concentration of nitrogens was 250 mM. Propylbromide, hexylbromide, nonylbromide and dodecylbromide (all from SIGMA) were dissolved in absolute ethanol at 250 mM and 3-bromopropanoic acid methyl ester, 6-bromohexanoic acid methyl ester, 8-bromooctanoic acid ethylester, 11-bromoundecanoic acid methyl ester or 16-bromohexadecanoic acid methyl ester were dissolved in absolute ethanol at 500 mM. $K_2CO_3$ was used as a 6 M solution in water.

For the modification of 100 μmol polyamine (based on monomer), the following solutions were pipetted per reaction:
  400 μl polyamine solution
  X μl of the ω-bromo carboxylic acid ester
  Y μl of the 1-bromoalkane
  wthanol up to 650 μl
  33 μl $K_2CO_3$ All mixtures were sealed and incubated for 7 days at 60° C. in an oven. Then, 250 μl of 2N NaOH were added, the mixtures were sealed again and incubated for another 2 days at 60° C. For initial tests, small aliquots of the reaction mixture were taken and diluted 1:100 in 75% ethanol/water. 42 μl of each diluted sample were transferred into a 96 well plate and dried.

Example 2

Complexation with siRNA

Modified polyamines were hydrated for 20 min in 50 μl of buffer pH4 (10 mM HAc, 10 mM $NaH_2PO_4$, pH4 with NaOH). 50 μl of a siRNA (2 μM in buffer pH4) were added and after 2-3 min the polymer-siRNA solution was brought to pH7 using 10 μl of 160 mM NaOH.

Example 3

Cultivation of Cells

HeLa cells were cultivated in 100 μl of RPMI1640 medium (PAA Lab GmbH) supplemented with 10% FCS (Sigma-Aldrich), 1× Pen/Strep (PAA lab GmbH) solution (according to the instructions of the manufacturer) and seeded at a density of 4000 cells/well in a 96 well-plate. The density of live cells was measured using the Countess Cell counter (Invitrogen). Cells were cultivated in a humidified incubator at 37° C. and 5% CO2. 24 h after plating cells were supplied with fresh complete medium and transfected the same day.

Example 4

Transfection of Cells

HeLa cells were transfected with the polyamine-siRNA-complexes by transferring 10 μl material as obtained under example 2 per well. This addition results in a concentration of 100 nM PLK-1 siRNA in the cell culture medium. Cells were cultivated for three days at 37° C. and 5% $CO_2$ in a humidified incubator without a change of the cultivation medium.

Example 5

Type of siRNA

The siRNA used here is targeting the PLK-1 gene, the product of which is an essential component in the cell cycle. Downregulation of the target protein results in mitotic arrest and apoptosis. The transfection of cells is therefore monitored using a cell viability assay. The siRNA targeting PLK-1 and an unrelated control siRNA used herein were published by Haupenthal et al. (2007) Int J Cancer, 121, 206-210.

Example 6

Viability Assay

Cells were tested for viability after three days by using the Cell Titer Blue assay (CTB, Promega). The medium was discarded and cells were supplied with fresh complete medium supplemented with the CTB reagent (5:1, vol/vol). 90-100 min after incubation at 37° C. and 5% CO2 in a humidified incubator the samples were transferred to a black fluorescence plate and color change of the samples was measured by a fluorescence reader at Ex560 nm/Em590 nm. The signal was normalized to 100% using untreated cells grown on the same culture plate and 0% with wells in which no cells were seeded.

Example 7

Transfection with Modified Polyamines

The following tables show the % of live cells relative to an untreated culture as a metric for the PLK-1 downregulation following cell transfection. In the experiment, carboxylated, alkylated and co-modified polyamines were tested in parallel.

TABLE 4

Transfection using carboxylated polyethylenimines

| | Eq. carboxyl[1] | 0 | 0.1 | 0.2 | 0.3 | 0.4 | 0.6 | 0.8 |
|---|---|---|---|---|---|---|---|---|
| PEI2k | C3 | 103 | 105 | 109 | 108 | 105 | 106 | 106 |
| | C6 | | 103 | 110 | 111 | 111 | 112 | 108 |
| | C8 | | 98 | 99 | 102 | 99 | 103 | 103 |
| | C11 | | 98 | 96 | 75 | 98 | 108 | 114 |
| | C16 | | 23 | 93 | 99 | 102 | 103 | 104 |
| PEI25k | C3 | 102 | 94 | 99 | 101 | 101 | 102 | 102 |
| | C6 | | 96 | 99 | 104 | 107 | 105 | 105 |
| | C8 | | 98 | 100 | 105 | 102 | 105 | 105 |
| | C11 | | 94 | 56 | 49 | 60 | 106 | 113 |
| | C16 | | 27 | 40 | 98 | 103 | 105 | 105 |
| bPEI | C3 | 79 | 92 | 94 | 91 | 97 | 104 | 102 |
| | C6 | | 93 | 94 | 91 | 92 | 109 | 107 |
| | C8 | | 85 | 90 | 92 | 93 | 103 | 101 |
| | C11 | | 44 | 43 | 30 | 67 | 102 | 105 |
| | C16 | | 56 | 106 | 104 | 106 | 107 | 107 |

[1]equivalents ω-bromo-carboxylic acid methyl ester added per nitrogen of the PEI polymer

TABLE 5

Transfection using alkylated polyethylenimines

| | Eq. alkyl[2] | 0 | 0.05 | 0.1 | 0.15 | 0.2 | 0.3 | 0.4 | 0.5 | 0.7 |
|---|---|---|---|---|---|---|---|---|---|---|
| PEI2k | C3 | 110 | 107 | 108 | 112 | 112 | 111 | 105 | 105 | 111 |
| | C6 | | 100 | 93 | 78 | 83 | 84 | 86 | 91 | 106 |
| | C9 | | 101 | 107 | 109 | 99 | 72 | 74 | 67 | 107 |
| | C12 | | 114 | 108 | 92 | 66 | 73 | 112 | 68 | 112 |
| PEI25k | C3 | 110 | 104 | 106 | 109 | 109 | 108 | 102 | 103 | 108 |
| | C6 | | 100 | 84 | 61 | 39 | 36 | 37 | 70 | 86 |
| | C9 | | 95 | 93 | 91 | 88 | 55 | 64 | 78 | 87 |
| | C12 | | 93 | 89 | 77 | 62 | 87 | 90 | 102 | 109 |
| bPEI | C3 | 88 | 94 | 94 | 87 | 93 | 88 | 92 | 91 | 85 |
| | C6 | | 70 | 55 | 53 | 57 | 57 | 55 | 71 | 102 |
| | C8 | | 45 | 43 | 55 | 55 | 78 | 79 | 99 | 104 |
| | C11 | | 78 | 80 | 93 | 104 | 105 | 108 | 107 | 107 |

[2]equivalents ω-bromoalkanes added per nitrogen of the PEI polymer

TABLE 6

Transfection using co-modified polyethylenimines

| | eq carboxyl + alkane[3] | 0 | 0.063 | 0.13 | 0.19 | 0.25 | 0.38 | 0.51 | 0.63 | 0.89 |
|---|---|---|---|---|---|---|---|---|---|---|
| PEI2k | C11⁻C3 | 94 | 93 | 99 | 97 | 98 | 102 | 100 | 106 | 106 |
| | C11⁻C6 | | 92 | 44 | 26 | 25 | 50 | 60 | 40 | 88 |
| | C11⁻C9 | | 95 | 72 | 31 | 20 | 19 | 40 | 26 | 85 |
| | C11⁻C12 | | 98 | 73 | 24 | 18 | 16 | 12 | 35 | 104 |
| PEI25k | C11⁻C3 | 96 | 90 | 90 | 90 | 90 | 82 | 64 | 87 | 100 |
| | C11⁻C6 | | 99 | 36 | 23 | 21 | 26 | 31 | 31 | 54 |
| | C11⁻C9 | | 84 | 30 | 24 | 23 | 21 | 26 | 29 | 52 |
| | C11⁻C12 | | 72 | 42 | 22 | 24 | 20 | 23 | 22 | 27 |
| bPEI | C11⁻C3 | 74 | 83 | 65 | 34 | 36 | 31 | 28 | 23 | 97 |
| | C11⁻C6 | | 48 | 39 | 27 | 29 | 25 | #NV | 52 | 97 |
| | C11⁻C9 | | 18 | 16 | 20 | #NV | #NV | 47 | 78 | 106 |
| | C11⁻C12 | | 34 | 26 | 29 | 28 | 22 | 26 | 50 | 104 |

[3]combined equivalents ω-bromo-undecanoic acid methyl ester and 1-bromoalkane added per nitrogen of the PEI polymer, ratio of ω-bromocarboxylic acid to bromoalkane 1.25:1

The polyethylenimines used here are essentially inactive transfectants under the assay conditions, only the branched PEI displays weak activity. Certain of the single modifications with either alkyl or carboxyl moieties yield improved activity and reductions of the cell viability below 50% are highlighted in the tables. The combined modifications with both carboxyalkyl and alkyl moieties display much greater activity on cells and the improvement is apparent for a wide range of DOS.

Example 8

Transfection Efficiency on Different Cell Types

Transfectant:

5 mmol of branched PEI was modified with 11-bromoundecanoic acid methyl ester and nonylbromid as described in example 1, all other reagents were brought to scale. The degree of substitution was about 40%, the ratio between the modifiers about 1. Modified Pei was purified from the reaction mixture using size exclusion chromatography in 10 mM NaOH, 70% ethanol.

Complexation:

Purified transfectant was provided in a solution containing 30% ethanol and 10 mM NaOH. Polymers were diluted in buffer D (10 mM citrate, adjusted to pH5.0 with NaOH) or buffer F (10 mM phosphate, adjusted to pH6.5 with NaOH) to a concentration of 4 mM. To obtain a NP-ratio of 10, 150 μl of the diluted polymers were complexed with 150 μl of 10 μM siRNA solution (Plk1 or scrambled control) in buffer D or F. Serial dilutions of these complexes were made in the respective buffers in a 96 well-plate to obtain concentrations from 500 nM to 2 nM on cells.

Transfection:

Cells were transfected with the polymer-siRNA-complexes by transferring a volume of 10 μl/well from the "complexation plate" to the cell plate (column 1-10). Cells were cultivated for three days at 37° C. and 5% CO2 in a humidified incubator without a change of the cultivation medium.

Viability Assay:

Cells were tested for viability after three days by using the Cell Titer Blue assay (CTB, Promega). The medium was discarded and cells were supplied with fresh complete medium supplemented with the CTB reagent (120 μl, 5:1, vol/vol). For NIH3T3, Jurkat and THP-1 cells the CTB-medium reagent was added directly to the cell medium, without discarding. 90-100 min (240 min for NIH3T3, Jurkat and THP-1 cells) after incubation at 37° C. and 5% CO2 in a humidified incubator the samples were transferred to a black fluorescence plate and color change of the samples was measured by a fluorescence reader at Ex560 nm/Em590 nm.

TABLE 7

List of cell types

| Name | Type | Species | Growth | Source |
|---|---|---|---|---|
| HeLa | Cervix-Carcinom | Human | adherent | DSMZ |
| HepG2 | Hepato-Carcinom | Human | adherent | CLS |
| Neuro 2a | Neuroblastom | Mouse | adherent | CLS |

The performance of the modified polyamine was measured as EC50, the concentration of siRNA needed for an inhibition of cell growth of 50%. In parallel, the same test was carried out using an unrelated siRNA and the EC50 value was also calculated. The signal-to-noise ratio is then defined as the ratio between the EC50 (control) and EC50 (PLK-1).

TABLE 8

Transfection and signal-to-noise ratio for a modified polyamine

| Cell type | EC50 (PLK-1, nM) | EC50 (CTR, nM) | Signal/Noise |
|---|---|---|---|
| HeLa | 3 | 27 | 9 |
| HepG2 | 54 | 145 | 3 |
| Neuro2A | 38 | 142 | 4 |
| CHO | 15 | 71 | 5 |

The data demonstrate a very efficient transfection of the siRNA into different cell types, including cell growing in suspension. The transfection reaction is very well tolerated by the cells with little or almost no signs of toxicity, indicated by signal-to-noise ratios of 3 or higher.

Example 9

Transfection Efficiency and Signal-to-Noise Ratio of Commercial Reagents

In the same experiment as described in example 8, several commercial transfectants were tested in parallel, the results of such test are listed in table 9.

Commercial Transfectants:

Interferin (Polyplus, France), Ribocellin (BioCellChallenge, Germany), TransIT-TKO (Mirus, US), siPort NeoFX (Ambion/Life technologies Corp.), Dharmafect (Dharmacon/Thermo Fisher) and Lipofectamine RNAiMAX (Invitrogen/Life Technologies Corp.) were handled and complexed to Plk1 and scr siRNA according to the manufacturer's instructions. Serial dilutions were made in Optimem I (Gibco/Life Technologies) to obtain siRNA concentrations from 100 nM to 2 nM on cells.

TABLE 9

Transfection and signal-to-noise ratio for commercial reagents

| | Reagent | | | | | | | |
|---|---|---|---|---|---|---|---|---|
| | siPort NeoFX | | | Dharmafect | | | RNAiMAX | | |
| | EC50 (nM) | | | EC50 (nM) | | | EC50 (nM) | | |
| Cell type | PLK | SCR | S/N | PLK | SCR | S/N | PLK | SCR | S/N |
| HeLa | 42 | >100 | 3 | 13 | 24 | 2 | 57 | 300 | 5 |
| HepG2 | 500 | 211 | 0 | 94 | 95 | 1 | 153 | 326 | 2 |
| Neuro | 500 | >500 | n.a. | 159 | 144 | 1 | 360 | 0 | 0 |
| CHO | >500 | >500 | n.a. | 13 | 27 | 2 | 43 | 204 | 5 |

Although transfection could be achieved in many cases in particular with the reagents Dharmafect and RNAiMAX, the signal-to-noise ratios are substantially lower throughout the test.

Example 10

Analytical Characterization

Transfectant:

5 mmol of branched PEI was modified with 11-bromoundecanoic acid methyl ester and nonylbromid as described in example 1, all other reagents were brought to scale. Alkylating reagents were added to target a degree of substitution was about 40%, the ratio between the modifiers about 1. Modified Pei was purified from the reaction mixture using size exclusion chromatography in 10 mM NaOH, 70% ethanol.

Analysis:

The estimated concentration of PEI was about 60 mM (based on monomer) at this point. 1 mL of the solution was mixed with 0.5 mL of 100 mM methoxyacetic acid and 25 µl of 2N NaOH. The mixture was dried under vacuum, dissolved in 700 µl CD3OD and analyzed by 1H NMR. Signals: methoxyacetic acid 4.0 ppm; bPEI backbone 2.4-2.7 ppm, terminal CH3 of the alkyl moiety 0.8 ppm and terminal CH2-COOH of the carboxyalkyl 2.1 ppm.

TABLE 10

Analysis of the 1H NMR spectrum

| Signal | | Example 10 | methoxy-acetic acid |
|---|---|---|---|
| Methoxyacetic acid | integral | | 2 |
| | µmol | | 100 |
| PEI backbone | integral | 4.8 | |
| | µmol | 120 | |
| —CH3 | integral | 0.7 | |
| | µmol | 23.33 | |
| | % of PEI | 19% | |
| —CH2—COOH | integral | 0.4 | |
| | µmol | 20 | |
| | % of PEI | 17% | |
| C/A | | 0.86 | |
| Total DOS | | 36% | |

Example 11

More Polyamine Derivatives

The following polyamines were subjected to the modification reaction outlined in example 1:

TABLE 11

Polyamines

| Polymer | Architecture | Molecular weight | Source |
|---|---|---|---|
| PEI (free base) | Linear | 2 kDa | Polysciences, Cat 24313 |
| PEI (free base) | Linear | 25 kDa | Polysciences, Cat 23966 |
| PEI (free base) | Linear | 100 kDa | Polysciences, Cat 25414 |
| PEI (free base) | Linear | 250 kDa | Polysciences, Cat 24314 |
| Polyethylenimine (free base) | Branched | 600 Da | Polysciences, Cat 02371 |
| Polyethylenimine (free base) | Branched | 1.2 kDa | Polysciences, Cat 06088 |

TABLE 11-continued

Polyamines

| Polymer | Architecture | Molecular weight | Source |
|---|---|---|---|
| Polyethylenimine (free base) | Branched | 1.8 kDa | Polysciences, Cat 06089 |
| PEI (free base) | Branched | 10 kDa | Aldrich, Cat 408727 |
| PEI (30% solution in water) | Branched | 70 kDa | Polysciences, Cat 06090 |
| PEI (50% solution in water) | Branched | 750 kDa | Polysciences, Cat 25448 |
| Poly-(N-methylvinylamine), free base | Linear | 500 kDa | Polysciences, Cat 24038 |
| Poly(allylamine), 15% solution in water | Linear | 15 kDa | Polysciences, Cat 24826 |

The polymers were dissolved in absolute ethanol at a concentration of 250 mono-mM; that is the concentration of nitrogen was 250 mM.

The carboxyl compounds for the modification of polyamines were chosen from the following table 12 and were dissolved in absolute ethanol at a concentration of 250 mM:

TABLE 12

Carboxyl compounds for the modification of polyamines.

| Carboxyl Compound | Symbol | Type | Source |
|---|---|---|---|
| 6-bromohexanoic acid methyl ester | C6 | Alkyl | Acros Organices 392690250 |
| 8-bromooctanoic acid ethylester | C8 | Alkyl | Nanjieng Pharmatechs HA-04H79 |
| 11-bromoundecanoic acid methyl ester | C11 | Alkyl | Aldrich 447463 |
| 16-bromohexadecanoic acid methyl ester | C16 | Alkyl | Aldrich 684511 |
| Methyl 4-(2-Bromoethyl) benzoate | CR1 | Aryl | Chempur 043959 |
| Methyl 4-(Bromomethyl) phenylacetate | CR2 | Aryl | ABCR AB246432 |
| Methyl 4-(2-Bromomethyl) benzoate | CR3 | Aryl | ABCR AB109915 |
| Methyl 3-(4-Bromomethyl) cinnamate | CR4 | Aryl | Combi-Blocks OR-2146 5 g |

The hydrophobic compounds for the modification of the polyamines were chosen from the following table 13 and were also dissolved in absolute ethanol at a concentration of 250 mM:

TABLE 13

Hydrophobic compounds for the modification of polyamines.

| Hydrophobic Compound | Symbol | Type | Source |
|---|---|---|---|
| Propylbromide | A3 | n-alkyl | SIGMA B78106 |
| Hexylbromide | A6 | n-alkyl | Aldrich B68240 |
| Nonylbromide | A9 | n-alkyl | Aldrich B74607 |
| Dodecylbromide | A12 | n-alkyl | Aldrich B65551 |
| Benzylbromide | BB | Aryl | SIGMA B17905 |
| 2-bromoethylbenzene | 2-BEB | Alkylaryl | SIGMA B65780 |
| 4-isopropylbenzylbromide | 4-IPBB | Alkylaryl | Aldrich 563285 |
| 1-bromo-2-cyclohexyl-ethane | B2CHE | Cyclic Alkyl | Aldrich 467952 |
| 3-(2-bromomethyl)-indole | 3-2-BEI | Heterocyclic Aryl | Aldrich 376523 |
| 1-(2-bromomethyl)-naphtaline | 1-2-BEN | Aryl | Aldrich 559318 |

$K_2CO_3$ was used as a 6 M solution in water.

For the modification of 100 μmol polyamine (based on monomer), the following solutions were pipetted per reaction:

400 μl polyamine solution
X μl of the ω-bromo carboxylic acid ester
Y μl of the brominated hydrocarbon compound
Absolute ethanol up to 650 μl
33 μl $K_2CO_3$ The combined amounts of X+Y were chosen for a degree of substitution of the amino groups of the polyamine between 0 and 100% and X and Y were further selected to complement each other and give various C/A ratios between 0 (only hydrophobic substituents) and the exclusive use of the carboxyl substituent, denoted as C/A=99 in the tables below.

All mixtures were sealed and incubated for 7 days at 60° C. in an oven. Then, 250 μl of 2N NaOH were added, the mixtures were sealed again and incubated for another 2 days at 60° C. For initial tests, small aliquots of the reaction mixture were taken and diluted 1:100 in 75% ethanol/water. 42 μl of each diluted sample were transferred into a 96 well plate and dried.

Example 12

Transfection of siRNA Using Modified Polyamines

The modified polyamines from example 11 were complexed with siRNA targeting PLK-1 and tested for their transfection properties as described in the examples 2 to 6 with the exception of using Buffer F (10 mM NaH2PO4, 225 mM sucrose, pH7.2 (adjusted with NaOH)) for siRNA complexation and transfection.

The results of the transfection reactions are described in the table 14 for modified polyamines where the hydrophobic moiety is an aliphatic or cyclic alkyle and in table 15 where said hydrophobic group is an aryle or alkylaryle.

TABLE 14 transfection of siRNA using certain polyamines wherein the lipophilic group is an alkyle. Lower numbers indicate successful transfection of the cells and are highlighted for values <=50.

| Polymer | Mol weight in KDa | Carbox. moiety | Hydrophobic moiety | DOS | 99 | 6 | 2.5 | 1.3 | 0.75 | 0.4 | 0.16 | 0 |
|---|---|---|---|---|---|---|---|---|---|---|---|---|
| lin PEI | 2 | C16 | A9 | 0.2 | 89 | 66 | 42 | 64 | 84 | 95 | 98 | 96 |
| | 2 | C16 | B2CHE | 0.2 | 104 | 43 | 43 | 98 | 103 | 106 | 109 | 107 |

TABLE 14-continued transfection of siRNA using certain polyamines wherein the lipophilic group is an alkyle. Lower numbers indicate successful transfection of the cells and are highlighted for values <=50.

| Polymer | Mol weight in KDa | Carbox. moiety | Hydro phobic moiety | DOS | % cell viability at certain C/A ratios | | | | | | | |
|---|---|---|---|---|---|---|---|---|---|---|---|---|
| | | | | | 99 | 6 | 2.5 | 1.3 | 0.75 | 0.4 | 0.16 | 0 |
| | 25 | C16 | A6 | 0.2 | 63 | 30 | 19 | 79 | 103 | 100 | 102 | 101 |
| | 25 | C16 | A9 | 0.2 | 93 | 59 | 36 | 61 | 84 | 104 | 105 | 103 |
| | 25 | C16 | B2CHE | 0.2 | 92 | 36 | 24 | 71 | 96 | 89 | 104 | 107 |
| | 100 | C16 | A9 | 0.2 | 84 | 34 | 46 | 76 | 97 | 92 | 96 | 101 |
| | 250 | C16 | A9 | 0.2 | 90 | 43 | 42 | 91 | 94 | 95 | 95 | 96 |
| bPEI | 0.6 | C16 | A12 | 0.5 | 75 | 72 | 70 | 62 | 62 | 66 | 51 | 79 |
| | 1.2 | C16 | A6 | 0.35 | 82 | 74 | 38 | 23 | 36 | 73 | 87 | 88 |
| | 1.2 | C16 | A9 | 0.35 | 83 | 89 | 47 | 24 | 23 | 63 | 50 | 80 |
| | 1.2 | C16 | B2CHE | 0.35 | 109 | 107 | 79 | 42 | 28 | 91 | 90 | 96 |
| | 1.8 | C16 | A9 | 0.35 | 104 | 101 | 95 | 94 | 66 | 41 | 73 | 91 |
| | 10 | C16 | A9 | 0.2 | 102 | 102 | 88 | 39 | 43 | 81 | 90 | 88 |
| | 10 | C11 | A9 | 0.35 | 91 | 88 | 78 | 58 | 32 | 54 | 95 | 103 |
| | 10 | C11 | A12 | 0.35 | 103 | 93 | 70 | 26 | 27 | 77 | 109 | 109 |
| | 10 | C11 | B2CHE | 0.5 | 86 | 88 | 85 | 88 | 49 | 53 | 21 | 91 |
| | 10 | C16 | B2CHE | 0.35 | 105 | 104 | 109 | 107 | 38 | 18 | 19 | 33 |
| | 70 | C16 | A9 | 0.35 | 99 | 88 | 81 | 58 | 49 | 29 | 29 | 91 |
| | 70 | C16 | B2CHE | 0.35 | 92 | 99 | 100 | 94 | 27 | 22 | 27 | 75 |
| | 750 | C11 | A12 | 0.35 | 100 | 58 | 24 | 46 | 50 | 97 | 90 | 94 |

The data of this table 14 demonstrate that many of the modified polyamines are capable of transfecting cells with siRNA. The hydrophobic group was selected from aliphatic or cyclic alkyl moieties and both resulted in the formation of active carriers regardless of their structural differences.

The active carriers were formed from polyamines having widely different molecular weights, and different architecture (linear or branched). It is also apparent from the data that the carboxyl and hydrophobic components act synergistically, while single modifications contribute little, if any, to the carrier properties.

TABLE 15 transfection of siRNA using certain polyamines wherein the hydrophobic group is an aryle, alkylaryl or heteroaryle.

| Polymer | mol weight in kDa | Carbox moiety | Hydro phobic moiety | DOS | % cell viability at certain C/A ratios | | | | | | | |
|---|---|---|---|---|---|---|---|---|---|---|---|---|
| | | | | | 99 | 6 | 2.5 | 1.3 | 0.75 | 0.4 | 0.16 | 0 |
| lin PEI | 2 | C16 | BB | 0.2 | 104 | 54 | 71 | 103 | 108 | 99 | 106 | 110 |
| | 2 | C16 | 2-BEB | 0.2 | 96 | 54 | 46 | 93 | 104 | 108 | 109 | 110 |
| | 2 | C16 | 4-IPBB | 0.2 | 99 | 37 | 82 | 102 | 104 | 103 | 102 | 110 |
| | 2 | C16 | 1-2-BEN | 0.2 | 99 | 58 | 52 | 97 | 93 | 92 | 100 | 104 |
| | 2 | C16 | 3-2 BEI | 0.2 | 101 | 67 | 74 | 103 | 102 | 93 | 101 | 106 |
| | 25 | C16 | BB | 0.2 | 103 | 88 | 76 | 104 | 109 | 104 | 96 | 108 |
| | 25 | C16 | 2-BEB | 0.2 | 68 | 26 | 31 | 84 | 96 | 97 | 100 | 112 |
| | 25 | C16 | 4-IPBB | 0.2 | 89 | 30 | 52 | 78 | 98 | 99 | 108 | 113 |
| | 25 | C16 | 1-2-BEN | 0.2 | 93 | 46 | 41 | 68 | 86 | 84 | 92 | 99 |
| | 25 | C16 | 3-2 BEI | 0.2 | 95 | 55 | 48 | 97 | 99 | 86 | 92 | 100 |
| bPEI | 1.2 | C16 | BB | 0.35 | 108 | 110 | 96 | 49 | 93 | 93 | 97 | 107 |
| | 1.2 | C16 | 2-BEB | 0.35 | 106 | 102 | 92 | 46 | 45 | 80 | 99 | 106 |
| | 1.2 | C16 | 4-IPBB | 0.35 | 107 | 104 | 76 | 44 | 45 | 34 | 31 | 80 |
| | 1.8 | C16 | BB | 0.35 | 105 | 104 | 100 | 50 | 30 | 72 | 78 | 104 |
| | 1.8 | C16 | 2-BEB | 0.35 | 105 | 98 | 95 | 84 | 43 | 77 | 85 | 109 |
| | 1.8 | C16 | 4-IPBB | 0.35 | 103 | 94 | 94 | 52 | 36 | 25 | 28 | 67 |
| | 10 | C16 | BB | 0.2 | 87 | 104 | 72 | 28 | 20 | 33 | 65 | 101 |
| | 10 | C16 | 2-BEB | 0.35 | 107 | 108 | 109 | 106 | 39 | 19 | 41 | 108 |
| | 10 | C11 | 4-IPBB | 0.2 | 94 | 86 | 85 | 73 | 42 | 21 | 25 | 45 |
| | 10 | C16 | 4-IPBB | 0.2 | 105 | 105 | 66 | 23 | 19 | 18 | 16 | 21 |
| | 10 | C16 | 1-2-BEN | 0.2 | 85 | 82 | 86 | 86 | 88 | 31 | 22 | 99 |
| | 10 | C16 | 3-2 BEI | 0.35 | 91 | 94 | 99 | 94 | 84 | 41 | 94 | 96 |
| | 70 | C16 | BB | 0.35 | 98 | 89 | 99 | 88 | 21 | 45 | 98 | 94 |
| | 70 | C16 | 2-BEB | 0.35 | 105 | 98 | 101 | 88 | 27 | 38 | 94 | 104 |
| | 70 | C16 | 4-IPBB | 0.35 | 101 | 99 | 99 | 86 | 44 | 30 | 19 | 76 |

The data of table 15 demonstrate that many of the modified polyamines are capable of transfecting cells with siRNA. The hydrophobic group was selected from aryle or alkylaryl moieties and all resulted in the formation of active carriers regardless of their structural differences.

The active carriers were formed from polyamines having widely different molecular weights, and different architecture (linear or branched). It is also apparent from the data that the carboxyl and hydrophobic components act synergistically, while single modifications contribute little, if any, to the carrier properties.

Example 13

Transfection of Plasmids

Cell culture: HeLa cells were cultivated in 100 μl of RPMI1640 medium (PAA Lab GmbH) supplemented with 10% FCS (Sigma-Aldrich), 1× Pen/Strep (PAA lab GmbH) solution (according to the manufacturer instructions) and seeded at 8000 cells/well of a 96 well-plate. Cells were cultivated in a humidified incubator at 37° C. and 5% CO2. 24 h after plating cells were supplied with fresh complete medium and transfected the same day.

Complexation: Polyamines were provided in 96 well plates, each well containing 3 mM polymer in 70% ethanol, Plasmid-DNA (pCMV-Luc) was provided as 0.011 μg/μl stock solution in Buffer F (10 mM NaH2PO4, 225 mM sucrose, pH7.2 (adjusted with NaOH)). 10 μl of polyamines were complexed with to 90 μl of Plasmid-DNA by mixing. 10-15 minutes after complexation, 10 μl of the mixture was used for transfection of HeLa cells resulting in 100 ng of Plasmid-DNA/well.

Determination of luciferase expression: Cells were prepared for quantitation of luciferase 24 h after transfection. Therefore, culture plates were equilibrated to room temperature for ca. 10 min. After discarding the medium cells were washed once with PBS. Cells were lysed using 100 μl of 1× Beetle Lysis Juice (PJK GmbH, Germany) and prepared for luminescence measurement 5 min later. Expression of luciferase was quantified using a TECAN luminescence plate reader.

Example 14

Results for the Transfection of Plasmids

The modified polyamines from example 11 were complexed with plasmid and tested for their transfection properties as described in example 13.

The results of the transfection reactions are described in the table 16 for modified polyamines where the lipophilic moiety is an aliphatic or cyclic alkyle; in table 17 where said lipophilic group is an aryle or alkylaryle and in table 18 where the carboxyl moiety comprises an aryl or alkylaryl.

TABLE 16 luminescence measured upon transfection of HeLa cells with a plasmid using certain polyamines wherein the hydrophobic group is an aliphatic alkyle. Signals lower than 100 light units were omitted for clarity, signals over 5000 light units are underlined.

| Polymer | mol weight in kDa | Carbox moiety | Hydro phobic moiety | DOS | luminescense signal at certain C/A ratios | | | | | | | |
|---|---|---|---|---|---|---|---|---|---|---|---|---|
| | | | | | 99 | 6 | 2 | 1.3 | 0.75 | 0.4 | 0.16 | 0 |
| lin PEI | 2 | C16 | A6 | 0.25 | | | 8.9E+02 | 4.8E+03 | 8.6E+03 | 3.6E+02 | | |
| | 2 | C16 | B2CHE | 0.25 | | | 1.1E+03 | 1.2E+03 | 2.3E+02 | 2.5E+03 | 2.7E+03 | |
| | 25 | C16 | A6 | 0.25 | | 1.3E+03 | 1.0E+04 | 1.6E+04 | 5.9E+03 | 1.1E+03 | 7.6E+02 | |
| | 25 | C6 | A9 | 0.25 | | | 3.7E+03 | 4.4E+04 | 4.0E+04 | 3.5E+04 | 2.6E+04 | |
| | 25 | C16 | B2CHE | 0.25 | | 1.4E+03 | 5.1E+03 | 3.3E+03 | 1.0E+04 | 4.1E+03 | 4.0E+04 | |
| | 100 | C16 | A3 | 0.25 | 3.9E+03 | 8.8E+04 | 6.3E+04 | 5.8E+04 | 1.1E+06 | 1.3E+06 | 2.2E+06 | 4.8E+03 |
| | 100 | C16 | A3 | 0.35 | 1.2E+02 | 3.7E+02 | 4.8E+03 | 4.3E+03 | 2.0E+05 | 1.8E+06 | 1.6E+05 | 1.5E+03 |
| | 100 | C11 | A3 | 0.25 | 7.3E+02 | 2.1E+03 | 4.0E+03 | 3.1E+03 | 1.1E+05 | 1.0E+05 | 3.8E+04 | 4.5E+03 |
| | 250 | C16 | A3 | 0.25 | | | 3.1E+03 | 4.2E+03 | 7.9E+03 | 5.4E+05 | 9.4E+05 | 8.4E+03 |
| | 250 | C16 | A3 | 0.35 | | | 2.3E+02 | 4.1E+04 | 1.5E+05 | 3.0E+05 | 4.1E+03 | |
| | 250 | C16 | A3 | 0.5 | | | | 1.6E+03 | 9.7E+04 | 1.2E+05 | 1.5E+03 | |
| | 250 | C16 | A6 | 0.25 | | | 2.4E+03 | 4.4E+04 | 6.4E+04 | 1.5E+04 | 6.1E+03 | 1.1E+04 | 5.4E+02 |
| | 250 | C11 | A3 | 0.25 | 4.6E+02 | 7.0E+03 | | 3.1E+02 | 3.0E+04 | 1.2E+05 | 5.6E+04 | 5.0E+04 |
| bPEI | 0.6 | C16 | A12 | 0.35 | | | | 2.5E+02 | 2.2E+04 | 9.0E+04 | 4.8E+02 | |
| | 0.6 | C11 | A12 | 0.5 | 3.9E+02 | 5.0E+02 | 3.4E+03 | 7.4E+03 | 1.4E+04 | 7.1E+04 | 5.1E+03 | 1.0E+04 |
| | 0.6 | C16 | B2CHE | 0.35 | | | 7.9E+02 | 4.0E+03 | 8.7E+03 | 1.6E+03 | | |
| | 1.2 | C11 | A9 | 0.35 | | | 1.2E+03 | 5.3E+03 | 7.3E+02 | 3.2E+04 | 7.4E+04 | 3.2E+04 | 6.8E+02 |
| | 1.2 | C11 | A12 | 0.35 | | | 1.8E+03 | 2.0E+04 | 4.4E+04 | 4.9E+05 | 1.3E+05 | 3.2E+04 | 6.5E+02 |
| | 1.2 | C11 | A12 | 0.5 | 1.7E+03 | 2.2E+04 | 5.9E+04 | 8.4E+04 | 1.5E+05 | 1.3E+05 | 2.8E+03 | |
| | 1.2 | C16 | A6 | 0.35 | | | 1.5E+03 | 3.4E+04 | 2.1E+04 | 1.2E+04 | 3.3E+03 | 3.2E+02 |
| | 1.2 | C16 | A9 | 0.35 | | | 2.4E+03 | 4.1E+03 | 3.0E+04 | 3.4E+04 | 3.8E+04 | 2.3E+02 |
| | 1.2 | C16 | A12 | 0.35 | | | 4.5E+02 | 1.6E+03 | 3.1E+03 | 4.5E+04 | 2.6E+04 | 1.0E+02 |
| | 1.2 | C16 | B2CHE | 0.35 | | 3.8E+02 | 3.1E+04 | 1.5E+05 | 1.3E+05 | 4.9E+04 | 1.8E+04 | 3.0E+03 |
| | 1.8 | C11 | A12 | 0.35 | 6.3E+02 | 5.6E+04 | 4.2E+04 | 2.6E+04 | 2.9E+05 | 2.5E+05 | 1.4E+04 | 1.0E+02 |
| | 1.8 | C16 | A6 | 0.35 | | 1.2E+02 | 7.6E+03 | 1.0E+05 | 9.8E+04 | 4.6E+04 | 7.1E+02 | |
| | 1.8 | C16 | A9 | 0.35 | | 2.3E+02 | 2.2E+03 | 7.7E+04 | 5.9E+04 | 4.1E+04 | 1.9E+04 | |
| | 1.8 | C16 | B2CHE | 0.35 | | 1.8E+03 | 8.0E+04 | 1.1E+05 | 7.5E+04 | 4.7E+04 | 1.5E+03 | |
| | 1.8 | C16 | A12 | 0.25 | | 7.9E+02 | 1.0E+03 | 3.8E+03 | 1.9E+04 | 8.5E+04 | 1.1E+04 | 1.3E+03 |
| | 10 | C6 | A6 | 0.35 | | 2.1E+02 | 6.7E+03 | 7.5E+04 | 2.2E+04 | 2.4E+03 | 6.6E+02 | 9.3E+02 |
| | 10 | C8 | A6 | 0.25 | | | 6.8E+03 | 1.1E+04 | 1.4E+04 | 1.2E+04 | 2.2E+03 | 5.3E+02 |
| | 10 | C11 | A9 | 0.35 | 9.4E+02 | 4.3E+03 | 2.6E+04 | 1.1E+04 | 4.8E+03 | 4.3E+03 | 1.2E+02 | |
| | 10 | C16 | B2CHE | 0.35 | | | 2.8E+02 | 8.2E+03 | 2.6E+04 | 1.4E+04 | 1.1E+03 | |
| | 70 | C6 | A6 | 0.35 | | | 2.1E+02 | 8.9E+04 | 2.0E+03 | 9.3E+02 | 4.3E+02 | |
| | 70 | C8 | A6 | 0.25 | 6.7E+02 | 4.3E+03 | 5.9E+04 | 2.6E+04 | 1.3E+04 | 2.2E+04 | 9.4E+02 | 1.7E+02 |
| | 70 | C11 | A9 | 0.35 | 7.0E+02 | 6.5E+03 | 1.8E+04 | 1.6E+04 | 1.4E+03 | 7.2E+03 | 4.5E+02 | |
| | 70 | C11 | A12 | 0.35 | 8.9E+02 | 4.2E+04 | 4.3E+04 | 1.2E+04 | 5.9E+03 | 3.5E+03 | 2.4E+02 | |
| | 70 | C16 | B2CHE | 0.35 | | | 5.0E+02 | 3.4E+03 | 4.4E+04 | 3.8E+04 | 1.7E+04 | 1.9E+03 |
| | 750 | C11 | A12 | 0.35 | | 9.1E+02 | 1.4E+04 | 7.6E+03 | 5.1E+03 | | | |

TABLE 16-continued luminescence measured upon transfection of HeLa cells with a plasmid using certain polyamines wherein the hydrophobic group is an aliphatic alkyle. Signals lower than 100 light units were omitted for clarity, signals over 5000 light units are underlined.

| Polymer | mol weight in kDa | Carbox moiety | Hydro phobic moiety | DOS | luminescense signal at certain C/A ratios | | | | | | |
|---|---|---|---|---|---|---|---|---|---|---|---|
| | | | | | 99 | 6 | 2 | 1.3 | 0.75 | 0.4 | 0.16 | 0 |
| poly-N- methyl vinyl- amine | 500 | C11 | A3 | 0.35 | | | 7.1E+02 | 2.2E+02 | | 3.3E+03 | | |
| | 500 | C11 | A6 | 0.35 | | | 3.9E+02 | | | | 1.1E+04 | |
| Poly- allyl- amine | 15 | C8 | A6 | 0.35 | | | 1.0E+03 | 3.6E+03 | | | | |
| | 15 | C11 | A6 | 0.25 | | | 1.7E+02 | 1.6E+03 | 8.5E+02 | 1.3E+03 | 4.3E+02 | |
| | 15 | C11 | B2CHE | 0.25 | | | | 1.0E+03 | 1.0E+03 | 1.7E+02 | 9.5E+03 | 2.1E+02 |

The data of this table 16 demonstrate that many of the carboxylated, hydrophobized polyamines are capable of transfecting a plasmid into cells. The hydrophilic group was selected from aliphatic or cyclic alkyl moieties and both resulted in the formation of active carriers regardless of their structural differences.

The active carriers were formed from polyamines having widely different molecular weights, different architecture (linear or branched) and different chemistry (polyethylenimines, polyallymine, polyvinylamine). It is also apparent from the data that the carboxyl and hydrophobic components act synergistically, while single modifications contribute little, if any, to the carrier properties.

The data of this table 17 demonstrate that many of the carboxylated, hydrophobized polyamines are capable of transfecting cells with a plasmid. The hydrophobic group was selected from aryle or alkylaryl moieties and all resulted in the formation of active carriers regardless of their structural differences.

The active carriers were formed from polyamines having widely different molecular weights, different architecture (linear or branched) and different chemistry (polyethylenimines, polyallymine). It is also apparent from the data that the carboxyl and hydrophilic components act synergistically, while single modifications contribute little, if any, to the carrier properties.

TABLE 17 transfection of a plasmid using certain polyamines wherein the hydrophobic group is an aryl or alkylaryl. Signals lower than 100 light units were omitted for clarity, signals over 5000 light units are underlined.

| Polymer | mol weight in kDa | Carbox moiety | Hydro phobic moiety | DOS | luminescense signal at certain ratios | | | | | | | |
|---|---|---|---|---|---|---|---|---|---|---|---|---|
| | | | | | 99 | 6 | 2.5 | 1.3 | 0.75 | 0.4 | 0.16 | 0 |
| lin PEI | 2 | C16 | BB | 0.25 | | 1.4E+02 | 6.7E+03 | 1.5E+04 | 1.1E+03 | | | |
| | 2 | C16 | 2-BEB | 0.25 | | 5.0E+02 | 4.2E+03 | 1.9E+03 | 2.1E+03 | 1.5E+03 | | |
| | 2 | C16 | 4-IPBB | 0.25 | | 5.9E+02 | 1.0E+04 | 6.4E+02 | 3.0E+02 | 1.2E+03 | 1.2E+03 | |
| | 2 | C16 | 1-2-BEN | 0.25 | | 3.2E+03 | 1.3E+04 | 3.5E+03 | 2.3E+03 | 5.5E+02 | | |
| | 25 | C16 | BB | 0.25 | | 1.4E+03 | 2.9E+04 | 3.2E+04 | | | | |
| | 25 | C16 | 2-BEB | 0.25 | | 2.9E+02 | 1.3E+04 | 2.9E+04 | 2.8E+04 | 2.0E+04 | 1.9E+03 | |
| | 25 | C16 | 4-IPBB | 0.25 | | 1.4E+03 | 1.8E+04 | 2.2E+03 | 1.7E+03 | 9.4E+02 | 1.6E+03 | |
| | 25 | C16 | 1-2-BEN | 0.25 | | 1.7E+02 | 1.5E+04 | 7.0E+04 | 4.3E+04 | 1.8E+04 | 1.9E+03 | 1.9E+02 |
| bPEI | 10 | C16 | BB | 0.35 | | | | | 4.0E+02 | 2.5E+04 | 2.3E+03 | |
| | 10 | C16 | 2-BEB | 0.35 | | | | | 6.3E+02 | 5.7E+03 | | |
| | 10 | C16 | 4-IPBB | 0.35 | | | | | | 9.0E+02 | 3.6E+03 | |
| | 10 | C16 | 1-2-BEN | 0.35 | | | | | 5.4E+02 | 5.2E+03 | 3.3E+03 | |
| | 70 | C16 | BB | 0.25 | 6.0E+03 | 6.3E+02 | 2.7E+04 | 8.4E+04 | 3.1E+04 | 1.1E+04 | 1.7E+02 | |
| | 70 | C16 | 2-BEB | 0.25 | | 1.3E+03 | 1.5E+04 | 1.9E+04 | 1.9E+04 | 4.5E+03 | 4.9E+03 | 2.3E+03 |
| | 70 | C16 | 4-IPBB | 0.25 | | 2.9E+03 | 4.4E+04 | 4.9E+04 | 3.5E+04 | 8.7E+03 | 3.6E+03 | 6.7E+03 |
| | 0.6 | C16 | BB | 0.35 | | | 2.8E+02 | 1.8E+04 | 3.8E+04 | 9.0E+03 | | |
| | 0.6 | C16 | 2-BEB | 0.35 | | | 2.4E+02 | 1.3E+04 | 1.8E+04 | 5.2E+02 | | |
| | 0.6 | C16 | 4-IPBB | 0.35 | | | 2.5E+03 | 3.3E+04 | 1.7E+04 | 2.7E+03 | 1.7E+03 | |
| | 1.2 | C16 | BB | 0.35 | 5.3E+02 | 4.6E+03 | 3.6E+04 | 3.1E+05 | 2.9E+05 | 1.2E+04 | 4.6E+03 | 3.3E+02 |
| | 1.2 | C16 | 2-BEB | 0.35 | | 2.7E+02 | 2.8E+04 | 1.1E+05 | 2.1E+05 | 3.0E+04 | 3.1E+02 | |
| | 1.2 | C16 | 4-IPBB | 0.25 | 2.1E+02 | 1.3E+04 | 7.2E+04 | 4.8E+04 | 3.2E+04 | 8.1E+03 | 2.7E+03 | 5.1E+02 |
| | 1.2 | C11 | 4-IPBB | 0.5 | | 7.2E+04 | 6.7E+04 | 5.0E+04 | 3.6E+04 | 5.0E+04 | 9.3E+03 | 5.4E+02 |
| | 1.8 | C16 | BB | 0.35 | | 5.8E+02 | 8.4E+03 | 8.1E+04 | 6.2E+05 | 4.0E+04 | 1.5E+03 | 5.2E+02 |
| | 1.8 | C16 | 2-BEB | 0.35 | | 1.3E+02 | 6.2E+03 | 1.1E+05 | 1.8E+05 | 1.6E+04 | 2.1E+02 | 6.9E+02 |
| | 1.8 | C16 | 4-IPBB | 0.35 | 3.1E+03 | 3.8E+02 | 9.9E+03 | 1.1E+05 | 9.6E+04 | 1.8E+04 | 1.6E+04 | |
| Poly- allyl- amine | 15.0 | C11 | BB | 0.25 | | | | | 9.2E+02 | 3.5E+04 | 1.4E+04 | 3.6E+03 |
| | 15.0 | C11 | 2-BEB | 0.25 | | 1.6E+02 | 1.6E+03 | | 1.7E+03 | 8.1E+02 | 4.8E+02 | 8.7E+02 |

TABLE 18 transfection of a plasmid using certain polyamines wherein the carboxyl group comprises an aryl or alkylaryl. Signals lower than 100 light units were omitted for clarity, signals over 5000 light units are underlined.

| Polymer | mol weight in KDa | Carbox moiety | Hydrophobic moiety | DOS | luminescense signal at certain ratios | | | | | | | |
|---|---|---|---|---|---|---|---|---|---|---|---|---|
| | | | | | 99 | 6 | 2.5 | 1.3 | 0.75 | 0.4 | 0.16 | 0 |
| lin PEI | 2 | CR1 | A9 | 0.25 | | | <u>2.3E+04</u> | <u>1.5E+04</u> | <u>7.4E+03</u> | <u>9.1E+03</u> | 2.0E+03 | 3.0E+02 |
| | 25 | CR1 | A3 | 0.25 | | | 1.0E+03 | 6.1E+02 | 2.0E+03 | 7.1E+02 | 1.4E+03 | 1.3E+03 |
| | 25 | CR1 | A9 | 0.25 | 4.8E+02 | <u>9.5E+03</u> | <u>8.7E+04</u> | <u>5.2E+04</u> | <u>2.1E+04</u> | <u>8.9E+03</u> | 1.1E+03 | |
| | 25 | CR1 | A12 | 0.25 | | <u>2.6E+04</u> | <u>1.4E+04</u> | 2.4E+03 | 3.3E+02 | 4.8E+02 | 3.8E+02 | |
| bPEI | 10 | CR1 | A3 | 0.25 | 8.4E+02 | | | 3.4E+03 | 3.4E+03 | 2.1E+03 | 9.1E+02 | 2.4E+02 |
| | 10 | CR1 | A6 | 0.25 | 1.7E+02 | 1.3E+03 | <u>5.7E+03</u> | 2.5E+03 | <u>1.8E+04</u> | <u>2.6E+04</u> | <u>8.2E+03</u> | 3.0E+03 |

The data of this table 18 demonstrate that many of the carboxylated, hydrophobized polyamines are capable of transfecting cells with a plasmid. The carboxyl group was selected from carboxylic acids comprising aryle or alkylaryl moieties and all resulted in the formation of active carriers regardless of their structural differences.

The active carriers were formed from polymers having widely different molecular weights or different architecture. It is also apparent from the data that the carboxyl and hydrophobic components act synergistically, while single modifications contribute little, if any, to the carrier properties.

Example 15

Synthesis of Various Carboxylated, Hydrophobized Oligospermines and Homologues Thereof Starting from commercially available 1,4-diamino butane (1) the central intermediate 21 was obtained in a three step synthesis.

Scheme 1: Synthetic route to the central intermediate 21.

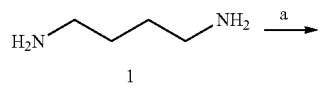

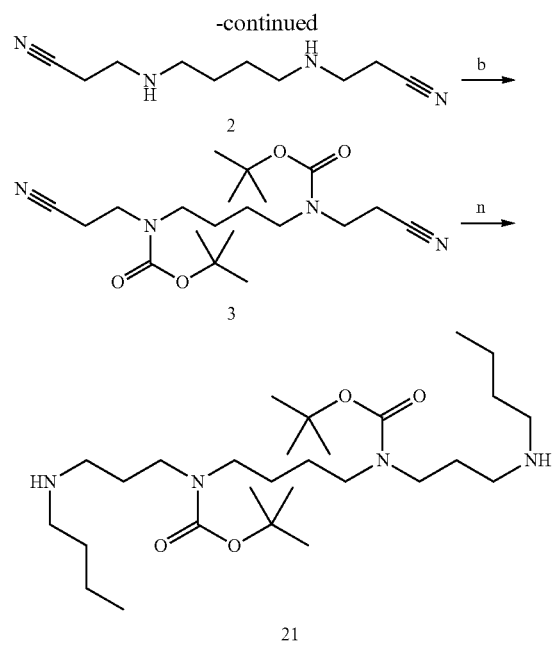

Compound 2 is easily accessible by addition of acrylonitrile to 1,4-diamino butane (1) in step a. Following this, two boc-protection groups were introduced into the molecule, leading to compound 3. The nitrile 3 was then reduced with hydrogen in the presence of excess butylamine to give 21.

Scheme 2: The oligomerization reaction
For the formation of oligospermins, 21 was reacted with 1,4-dichlorobut-2-in under standard alkylation conditions to give dimer 41, trimer 42 and a series of longer oligomers:
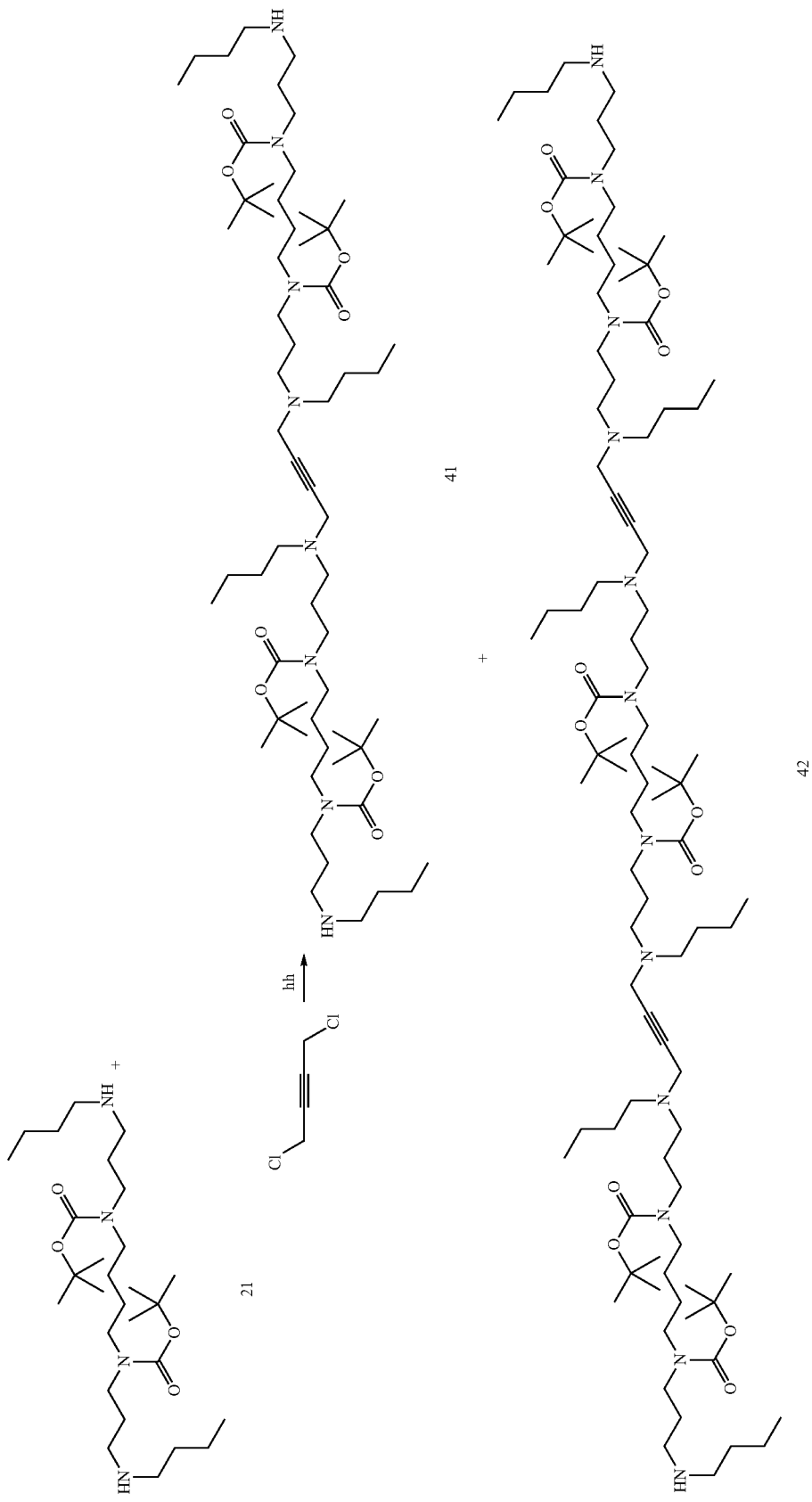

Unfortunately, the N—CH$_2$—C≡C moiety is not stable and susceptible to cleavage. Therefore, the triple bond of compounds 41, 42 or the higher oligomers were reduced followed by removal of the Boc-groups.

Analogue reactions were carried out using 1,5-diaminopentane or 1,6-diaminohexane as the starting material 1, leading to a series of oligospermine homologues or polyalkylenimines wherein the variable x denoting the spacing between the nitrogen groups oscillates between 2 and 3, 2 and 4, or 2 and 5.

In addition to the formation of the oligospermine homologues, the size of the hydrophobic substituents was systematically varied between butyl (as illustrated in this example), ethyl, hexyl and decyl, yielding a matrix of different polyalkylenimines having variations in their alkylen groups, their hydrophobic substituents and their degree of oligomerization.

The oligospermines and their homologues (altogether the polyalkylenimines of this example) were desalted using Sephadex G25 and the individual oligomers were purified using ion exchange chromatography on CM-Sepharose Fast Flow and SP-Sepharose Fast Flow. The oligospermines elute from the ion exchange column according to their degree of polymerization and are denoted with roman numerals I to XII, whereby higher numbers stand for longer oligomers. The degree of polymerization was determined with mass spectroscopy and ranged from trimers through to about eicosamers.

Fractions containing the separated oligomers were extracted from the buffer using dichlormethan under basic conditions, dried under vacuum and dissolved in absolute ethanol at a concentration of 250 mM nitrogen.

In a subsequent step, samples of 50 µmol of each oligomer were derivatized with 0, 10, 15, 20 or 25 µmol of the ω-bromocarboxylic acids C3, C6, C8, C11 and C16 using the general protocol of example 11.

Example 16

Transfection of Cells Using Carboxyl-Hydrocarbon-Oligospermines

The transfection testing of the various carboxylated and hydrophobized oligospermines and their respective homologues was performed using the siRNA targeting PLK-1, the HeLa cells and the cell culture conditions and assays described in the examples 2 to 7.

The following table 19 is a list of the results obtained using the carboxyl-hydrocarbon-oligospermines as transfectants for siRNA.

TABLE 19

Inhibition of the cell viability of HeLa cells upon transfection of a cytotoxic siRNA using carboxylated, hydrophobized oligospermines. Numerals x denote the oscillating lengths of the alkylen units according to formula (1), the roman numerals for the oligomers denote the degree of polymerization of the oligomers. The numbers in the table show the remaining cell viability, low numbers indicate an efficient transfection.

| | | % substitution with C11 | | | | | % substitution with C16 | | | | |
|---|---|---|---|---|---|---|---|---|---|---|---|
| x alkyl | oligomer | 0 | 20 | 30 | 40 | 50 | 0 | 20 | 30 | 40 | 50 |
| 2; 4 butyl | III | 105 | 87 | 81 | 79 | 70 | 100 | 31 | 39 | 34 | 37 |
| | IV | 91 | 56 | 63 | 32 | 37 | 99 | 25 | 36 | 26 | 29 |
| | V | 77 | 81 | 83 | 81 | 15 | 79 | 80 | 76 | 47 | 41 |
| | VI | 100 | 101 | 98 | 100 | 99 | 98 | 101 | 102 | 101 | 105 |

TABLE 19-continued

Inhibition of the cell viability of HeLa cells upon transfection of a cytotoxic siRNA using carboxylated, hydrophobized oligospermines. Numerals x denote the oscillating lengths of the alkylen units according to formula (1), the roman numerals for the oligomers denote the degree of polymerization of the oligomers. The numbers in the table show the remaining cell viability, low numbers indicate an efficient transfection.

| | | % substitution with C11 | | | | | % substitution with C16 | | | | |
|---|---|---|---|---|---|---|---|---|---|---|---|
| x alkyl | oligomer | 0 | 20 | 30 | 40 | 50 | 0 | 20 | 30 | 40 | 50 |
| 2; 5 butyl | II | 77 | 70 | 79 | 83 | 13 | 82 | 82 | 71 | 49 | 37 |
| 2; 3 hexyl | I | 51 | 61 | 72 | 35 | 2 | 57 | 29 | 27 | 56 | 67 |
| | II | 85 | 95 | 92 | 35 | 31 | 90 | 63 | 47 | 79 | 52 |
| | III | 82 | 88 | 104 | 37 | 23 | 107 | 40 | 40 | 64 | 55 |
| | IV | 86 | 44 | 84 | 41 | 27 | 64 | 33 | 29 | 62 | 97 |
| | V | 100 | 79 | 91 | 34 | 35 | 101 | 75 | 43 | 54 | 88 |
| | VI + VII | 80 | 82 | 81 | 84 | 87 | 85 | 85 | 86 | 88 | 87 |
| | VIII + IX | 93 | 92 | 87 | 48 | 5 | 102 | 93 | 69 | 92 | 23 |
| | X | 54 | 37 | 0 | 0 | 2 | 73 | 24 | 1 | 2 | 2 |
| | XI | 19 | 0 | 0 | 1 | 4 | 102 | 68 | 94 | 85 | 83 |
| | XII | 62 | 70 | 63 | 28 | 11 | 104 | 71 | 104 | 92 | 37 |
| 2; 4 hexyl | II | 102 | 108 | 97 | 84 | 106 | 102 | 103 | 105 | 57 | 60 |
| | III | 87 | 104 | 89 | 39 | 43 | 90 | 97 | 65 | 81 | 56 |
| | IV | 100 | 105 | 90 | 81 | 43 | 95 | 82 | 79 | 66 | 52 |
| | VI | 98 | 94 | 93 | 86 | 86 | 96 | 0 | 2 | 93 | 89 |
| | VII | 100 | 93 | 93 | 88 | 88 | 70 | 58 | 23 | 74 | 90 |
| | VIII | 30 | 59 | 0 | 3 | 34 | 17 | 39 | 23 | 7 | 61 |
| | XI | 104 | 100 | 104 | 104 | 104 | 107 | 107 | 110 | 112 | 109 |
| | X | 84 | 85 | 73 | 31 | 13 | 62 | 46 | 16 | 53 | 53 |
| | IX | 101 | 97 | 84 | 88 | 88 | 30 | 26 | 12 | 80 | 96 |
| 2; 5 hexyl | III | 104 | 77 | 49 | 2 | 31 | 36 | 7 | 73 | 60 | 92 |
| | IV | 110 | 105 | 89 | 98 | 108 | 103 | 89 | 68 | 43 | 70 |
| | V | 92 | 83 | 67 | 24 | 39 | 87 | 64 | 59 | 42 | 35 |
| | VI | 97 | 93 | 97 | 99 | 96 | 99 | 99 | 96 | 100 | 99 |
| 2; 3 decyl | II + III | 102 | 86 | 78 | 94 | 93 | 104 | 105 | 105 | 113 | 104 |
| | VI | 107 | 108 | 95 | 88 | 79 | 109 | 108 | 109 | 109 | 119 |
| | VII | 109 | 99 | 69 | 80 | 92 | 105 | 108 | 113 | 108 | 119 |
| | VIII | 109 | 2 | 6 | 92 | 13 | 107 | 105 | 107 | 111 | 106 |
| | IX | 109 | 111 | 108 | 108 | 107 | 104 | 104 | 104 | 103 | 106 |

The data of this table 19 demonstrate that many of the carboxylated, hydrophobized oligospermines are capable of transfecting cells. The active carriers were formed from oligospermines having widely different molecular weights and are of different molecular architecture as the spacing between the nitrogen atoms was varied. It is also apparent from the data that the carboxyl and hydrophobic components act synergistically, as the alkylated oligospermins display little, if any activity in the cell transfection while the introduction of the carboxyl moieties lead to active carrier structures.

Example 17

Neutral and Anionic Particles from Modified Polyamines and Nucleic Acid

Buffers containing 280 mM sucrose, 10 mM sodium dihydrogenphosphate and 3 mM sodium hydroxide (pH6.5) or 7 mM sodium hydroxide (pH7.2) was prepared. Stock solutions of the siRNA from example 5 were prepared in the buffers to obtain 10 fold the concentrations listed in table 20.

The modified polyamine of example 8 was provided as a solution having a concentration of 56 mM modified polyamine (as mono-mM) in 70% ethanol, 10 mM sodium hydroxide; 50 µl of said solution of the modified polyamine were rapidly mixed with 4.1 ml of either buffer. A colloid forms and the particle size and the zeta potential of the dispersed phase were determined using MALVERN Zetasizer 3000 HSA.

900 μl of the various siRNA solutions were rapidly mixed with the dispersions of the modified polyamine in buffer so to obtain the N/P ratios listed in table 20 and size and zeta potential were recorded again.

TABLE 20

Size and zeta potential of complexes between a modified polyamine and siRNA having various ratios of N/P.

| polyamine [μM] | siRNA [μM] | N/P | pH 6.5 | | pH 7.2 | |
|---|---|---|---|---|---|---|
| | | | Size [nm] | Zeta potential [mV] | Size [nm] | Zeta potential [mV] |
| 560 | 6.2 | 2 | 496 | −29.5 | 503 | −32.5 |
| 560 | 3.1 | 4 | 537 | −30.2 | 519 | −29.2 |
| 560 | 2.1 | 6 | 858 | −7.5 | 546 | −34.9 |
| 560 | 1.4 | 9 | 1268 | 2.8 | 1292 | −1.5 |
| 560 | 1.04 | 12 | 857 | 2.1 | 615 | 0.1 |
| 560 | 0.83 | 15 | 656 | 2.1 | 606 | 0.4 |
| 560 | 0.62 | 20 | 521 | −0.3 | 625 | 1.5 |
| 560 | 0.41 | 30 | 516 | 2.3 | 596 | 1.3 |
| 560 | 0 | 99 | 532 | 2.1 | 538 | 1.8 |

General observations: the modified polyamines do from particles having a size of about 500 nm and an almost neutral zeta potential. Addition of small amounts of siRNA resulting in N/P ratios of 12 or higher do not substantially alter the size or surface charge of the particles. However, addition of larger amounts of siRNA led to the formation of anionic particles of about the same size. Intermediate amounts of siRNA lead to intermediate zeta potential and the formation of aggregates. The systems behavior can be understood as the interaction of two polyelectrolytes of opposite charge, where aggregation occurs under the conditions of charge neutralization as described in Endert et al. (2004) "Nanocapsules from liposomal templates", pp. 238-248 in Carrier Based Drug Delivery, Oxford University Press. Specific observations: At pH6.5 the charge reversal towards the fully anionic state requires a N/P of 4, whereas the same process is completed at N/P6 at a pH of 7.2. This observation is in line with the stronger ionization of the PEI backbone amines at lower values of pH.

Example 18

Lyophilization of Transfectants

The modified polyamine from Example 8 was provided as solution in 70% ethanol, 10 mM sodium hydroxide having a concentration of 56 mM nitrogen. Various amounts of the clear solution of the transfectant were rapidly injected into a homogenous phase comprising 280 mM sucrose and 20 mM sodium phosphate adjusted with NaOH to pH 6.5 so that the final concentration of transfectant was 0.15 mM or 0.03 mM. The mean particles sizes and polydispersities were 389 nm (PI of 0.09) and 332 nm (PI of 0.11) for the samples having 0.15 mM or 0.03 mM nitrogen, respectively.

Aliqouts of 100 μl each were placed in 96 well plates. The materials were frozen for 4 hours at −18° C. and transferred into a freeze-dryer. Lyophilization occurred at a constant pressure of 0.12 mbar for 20 hours. After removal from the lyophilization chamber, the plates were quickly sealed using a heat sealer.

One the next day, seals were broken and the samples were rehydrated with water. The lyophilized product dissolved quickly and homogeneously. Particle size and polydispersity were determined as above.

Within 15 minutes after starting rehydration, the resulting colloidal transfectants had a mean particle size of 423 nm (PI 0.13) when 15 nmol of transfectant were placed in each well. The resulting colloidal transfectants had a mean particle size of 356 nm (PI 0.12) when 3 nmol of transfectant were placed in each well.

The content of European patent application No. 12 006 963.8, filed on Oct. 8, 2012, the priority of which is claimed, is herewith incorporated by reference including all claims and entire description.

The invention claimed is:

1. A polyalkylenimine derivative for the transfection of polyanions into cells comprising:
   a plurality of carboxylated substituents comprising a carboxyl group bonded via a hydrophobic linker to amino groups of a polyalkylenimine, wherein each of said carboxylated substituents comprises from 6 to 40 carbon atoms, preferably from 6 to 20 carbon atoms, and more preferably from 8 to 16 carbon atoms; and
   a plurality of hydrophobic substituents bonded to amino groups of said polyalkylenimine, wherein each of said hydrophobic substituents comprises at least 2 carbon atoms.

2. The polyalkylenimine derivative of claim 1, wherein any one or more of said hydrophobic linkers comprises from 1 to 3 heteroatoms selected from O, N, and S.

3. The polyalkylenimine derivative of claim 1, wherein any one or more of said hydrophobic substituents comprises from 1 to 3 heteroatoms selected from O, N, and S provided said hydrophobic substituent has at least 6 carbon atoms.

4. The polyalkylenimine derivative of claim 1 further being complexed to a nucleic acid or a protein.

5. The polyalkylenimine derivative of claim 1 wherein each of said hydrophobic substituents comprises from 6 to 40 carbon atoms.

6. The polyalkylenimine derivative according to claim 1, wherein said carboxylated substituents are carboxyalkyl substituents and said hydrophobic substituents are alkyl substituents.

7. The polyalkylenimine derivative according to claim 6, wherein the number of carbon atoms of said carboxyalkyl substituent together with the number of carbon atoms of said alkyl substituent is between 10 and 30.

8. The polyalkylenimine derivative according to claim 7, wherein the number of carbon atoms of said carboxyalkyl substituent together with the number of carbon atoms of said alkyl substituent is between 15 and 25.

9. The polyalkylenimine derivative according to claim 6, wherein a uniform carboxyalkyl substituent and no mixture of different carboxyalkyl substituents is used and wherein a uniform alkyl substituent and no mixture of alkyl substituents is used.

10. The poylalkylenimine derivative according to claim 9, wherein the number of carbon atoms of said uniform carboxyalkyl substituent together with the number of carbon atoms of said uniform alkyl substituent is between 10 and 30, preferably between 15 and 25.

11. The poylalkylenimine derivative according to claim 10, wherein the number of carbon atoms of said uniform carboxyalkyl substituent together with the number of carbon atoms of said uniform alkyl substituent is between 15 and 25.

12. A polyvinylamine derivative for the transfection of polyanions into cells, comprising:
   a plurality of carboxylated substituents comprising a carboxyl group bonded via a hydrophobic linker to amino groups of a polyvinylamine, wherein each of said carboxylated substituents comprises from 6 to 40 carbon atoms; and a plurality of hydrophobic substituents bonded to amino groups of said polyvinylamine, wherein each of said hydrophobic substituents comprises at least 2 carbon atoms, preferably from 6 to 40 carbon atoms.

13. The polyvinylamine derivative of claim 12 wherein each of said carboxylated substituents comprises from 6 to 20 carbon atoms.

14. The polyvinylamine derivative of claim 13 wherein each of said carboxylated substituents comprises from 8 to 16 carbon atoms.

15. The polyvinylamine derivative of claim 12 wherein each of said hydrophobic substituents comprises from 6 to 40 carbon atoms.

16. The polyvinylamine derivative of claim 12, wherein any one or more of said hydrophobic linkers comprises from 1 to 3 heteroatoms selected from O, N, and S.

17. The polyvinylamine derivative of claim 12, wherein any one or more of said hydrophobic substituents comprises from 1 to 3 heteroatoms selected from O, N, and S provided said hydrophobic substituent has at least 6 carbon atoms.

18. A polyallylamine derivative for the transfection of polyanions into cells, comprising:

a plurality of carboxylated substituents comprising a carboxyl group bonded via a hydrophobic linker to amino groups of a polyallylamine, wherein each of said carboxylated substituents comprises from 6 to 40 carbon atoms; and a plurality of hydrophobic substituents bonded to amino groups of said polyallylamine, wherein each of said hydrophobic substituents comprises at least 2 carbon atoms.

19. The polyallylamine derivative of claim 18 wherein each of said carboxylated substituents comprises from 6 to 20 carbon atoms.

20. The polyallylamine derivative of claim 19 wherein each of said carboxylated substituents comprises from 8 to 16 carbon atoms.

21. The polyallylamine derivative of claim 18 wherein each of said hydrophobic substituents comprises from 6 to 40 carbon atoms.

22. The polyallylamine derivative of claim 18, wherein any one or more of said hydrophobic linkers comprises from 1 to 3 heteroatoms selected from O, N, and S.

23. The polyallylamine derivative of claim 18, wherein any one or more of said hydrophobic substituents comprises from 1 to 3 heteroatoms selected from O, N, and S provided said hydrophobic substituent has at least 6 carbon atoms.

* * * * *